(12) United States Patent
Ito et al.

(10) Patent No.: US 8,911,405 B2
(45) Date of Patent: Dec. 16, 2014

(54) NEEDLE DEVICE

(75) Inventors: Toru Ito, Hiroshima (JP); Mamoru Kohno, Hiroshima (JP); Ryoji Fujii, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 97 days.

(21) Appl. No.: 13/508,244

(22) PCT Filed: Nov. 18, 2010

(86) PCT No.: PCT/JP2010/070603
§ 371 (c)(1),
(2), (4) Date: May 4, 2012

(87) PCT Pub. No.: WO2011/074372
PCT Pub. Date: Jun. 23, 2011

(65) Prior Publication Data
US 2012/0220943 A1    Aug. 30, 2012

(30) Foreign Application Priority Data

Dec. 14, 2009  (JP) .................................. 2009-283017
Dec. 14, 2009  (JP) .................................. 2009-283018

(51) Int. Cl.
*A61M 5/178* (2006.01)
*A61M 5/36* (2006.01)
*A61M 5/32* (2006.01)
*A61M 5/34* (2006.01)
*A61M 25/06* (2006.01)

(52) U.S. Cl.
CPC ............ *A61M 5/36* (2013.01); *A61M 25/0631* (2013.01); *A61M 5/3293* (2013.01); *A61M 5/34* (2013.01)
USPC .................................................. 604/164.08

(58) Field of Classification Search
CPC ........ A61M 5/3293; A61M 5/34; A61M 5/36
USPC ........................................ 604/164.01–164.13
See application file for complete search history.

(56) References Cited

U.S. PATENT DOCUMENTS

| | | | |
|---|---|---|---|
| 5,893,844 A | | 4/1999 | Misawa |
| 7,682,339 B2 * | | 3/2010 | Fujii ......................... 604/164.08 |
| 2008/0108944 A1 * | | 5/2008 | Woehr et al. ............. 604/164.08 |

FOREIGN PATENT DOCUMENTS

| | | |
|---|---|---|
| EP | 1 862 193 | 12/2007 |
| EP | 1 980 284 | 10/2008 |

(Continued)

*Primary Examiner* — Quynh-Nhu H Vu
*Assistant Examiner* — Jenna Zhang
(74) *Attorney, Agent, or Firm* — Hamre, Schumann, Mueller & Larson, P.C.

(57) ABSTRACT

An inner hub (9) with a needle attached to a tip thereof is housed in a cylindrical body (2). The inner hub (9) includes a through-hole (22) penetrating the inner hub (9) in a radial direction of the inner hub (9), and a recessed portion (23*a*) formed in an outer circumferential surface (23) of the inner hub (9). An opening of the through-hole (22) and the recessed portion (23*a*) are connected together in a circumferential direction of the inner hub (9). A liquid flowing out from the opening of the through-hole (22) is limited so that the liquid flows along the recessed portion (23*a*), and the flow of the liquid moving in the circumferential direction of the inner hub (9) is promoted. As a result, the removal of air bubbles in the circumferential direction of the inner hub (9) is promoted, whereby air bubbles can be prevented from remaining on the outer circumferential surface (23) of the inner hub (9).

10 Claims, 20 Drawing Sheets

(56) References Cited

FOREIGN PATENT DOCUMENTS

| | | |
|---|---|---|
| JP | 10-258123 | 9/1998 |
| JP | 2006-297062 | 11/2006 |
| JP | 2006297062 A * | 11/2006 |
| WO | 2007/083770 | 7/2007 |

* cited by examiner

NEEDLE DEVICE

This application is a National Stage Application of PCT/JP2010/070603, filed Nov. 18, 2011, which claims priority to JP Application No. 2009-283017, filed Dec. 14, 2009, and JP Application No. 2009-283018, filed Dec. 14, 2009.

TECHNICAL FIELD

The present invention relates to a needle device in which an inner hub with a needle integrated therewith is provided in a cylindrical body.

BACKGROUND ART

Among known medical needle devices are, for example, indwelling needle devices, which are used for infusion and blood transfusion. A known indwelling needle device is one in which a needle portion projecting from a tip of a cylindrical body has a double structure including a soft outer needle and a hard inner needle (see Patent Documents 1 and 2).

In such an indwelling needle device, when the hard inner needle which has been caused to project from the soft outer needle is inserted into a patient's arm etc., the soft outer needle is also inserted along with the hard inner needle. Thereafter, the hard inner needle is pulled into the cylindrical body, whereby only the soft outer needle is left at the insertion site. As a result, even when the patient moves, pain at the insertion site can be relieved and damage to a blood vessel can be prevented.

The hard inner needle is integrated with the inner hub to which a tube is connected. By pulling the tube, the inner hub is moved, so that the hard inner needle integrated with the inner hub is pulled into the cylindrical body.

In the above indwelling needle device, a drug solution etc. is supplied through the tube to the inner hub connected to the tube and then passed through the soft outer needle before being administered into a patient. When the drug solution etc. is administered, if air is present in the indwelling needle device, the air enters a blood vessel along with the drug solution etc.

Therefore, prior to insertion, the indwelling needle device is filled with a liquid, such as physiological saline, a nutrient solution, etc. This operation is called priming.

CITATION LIST

Patent Documents

Patent Document 1: JP 2006-297062A
Patent Document 2: WO/2007/083770 (a domestic publication of a PCT international publication)

DISCLOSURE OF INVENTION

Problem to be Solved by the Invention

However, in the above conventional indwelling needle device, even if the priming operation is performed, it may be difficult to remove air bubbles from the indwelling needle device. This is because the liquid injected into the indwelling needle device is discharged through the inner hub. Specifically, the injected liquid temporarily flows into the inner hub, flows out of the inner hub through a hole formed in the inner hub, and passes through a gap between an outer circumferential surface of the inner hub and the cylindrical body, before reaching the outer needle. During this process, the liquid may not reach or spread sufficiently over the outer circumferential surface of the inner hub, and therefore, air bubbles may continue to remain on the outer circumferential surface of the inner hub.

The present invention has been made to solve the above conventional problem. It is an object of the present invention to provide a needle device that can prevent air bubbles from remaining on the outer circumferential surface of the inner hub.

Means for Solving Problem

A first needle device according to the present invention includes an inner hub with a needle attached to a tip thereof, and a cylindrical body housing the inner hub. The inner hub includes a through-hole penetrating the inner hub in a radial direction of the inner hub, and a recessed portion formed in an outer circumferential surface of the inner hub. An opening of the through-hole and the recessed portion are connected together in a circumferential direction of the inner hub.

A second needle device according to the present invention includes an inner hub with a needle attached to a tip thereof, and a cylindrical body housing the inner hub. The inner hub includes a through-hole penetrating the inner hub in a radial direction of the inner hub, and a protrusion formed between an opening of the through-hole and the tip of the inner hub and protruding from an outer circumferential surface of the inner hub.

Effects of the Invention

According to the present invention, air bubbles can be prevented from remaining on the outer circumferential surface of the inner hub.

DESCRIPTION OF THE INVENTION

Figure 1:
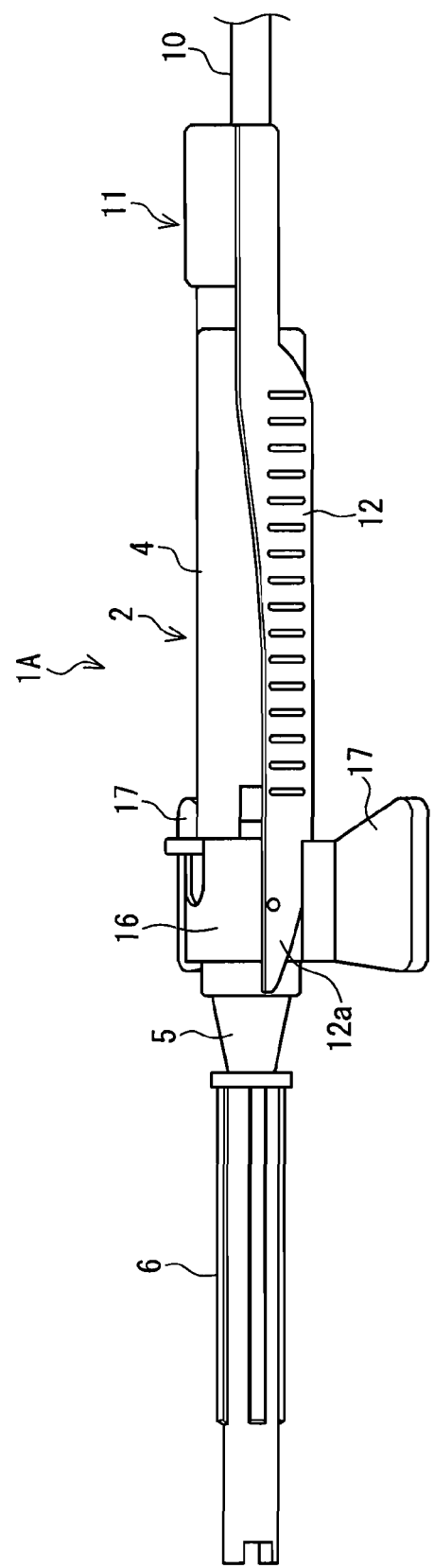
FIG. 1 is a perspective view of the external appearance of an indwelling needle device 1A according to a first embodiment of the present invention.

According to the first needle device of the present invention, the recessed portion connected to the opening of the through-hole in the circumferential direction of the inner hub is formed in the outer circumferential surface of the inner hub. Therefore, the flow of a liquid flowing out from the opening of the through-hole is limited so that the liquid flows along the recessed portion, whereby the flow of the liquid moving in the circumferential direction of the inner hub can be promoted. As a result, the removal of air bubbles in the circumferential direction of the inner hub is promoted. Therefore, according to the present invention, when a liquid is injected into the needle device in the priming operation, air can be replaced reliably with the liquid, whereby air bubbles can be prevented from remaining on the outer circumferential surface of the inner hub.

In the first needle device of the present invention, the recessed portion is preferably arranged to guide a liquid flowing out from the opening of the through-hole in the circumferential direction of the inner hub.

The opening of the through-hole is preferably interposed between the recessed portions in the circumferential direction of the inner hub. This configuration is advantageous for promoting the removal of air bubbles in the circumferential direction of the inner hub.

The recessed portions are preferably separated from each other by a separator surface serving as a boundary, and preferably include a portion whose depth becomes gradually shallower in a direction from the opening of the through-hole to the separator surface. This configuration allows air bubbles to move more easily up onto the top of the separator surface along with the liquid and then flow toward the tip of the inner hub. Thus, this configuration is advantageous for promoting the removal of air bubbles.

The recessed portion preferably includes a portion extending in an axial direction of the inner hub. This configuration is advantageous for promoting the removal of air bubbles in the axial direction of the inner hub.

The width of the recessed portion is preferably smaller than or equal to one half of the length of the opening of the through-hole in an axial direction of the inner hub. With this configuration, the flow of the liquid is concentrated into a portion in which air bubbles are likely to remain. Thus, this configuration is advantageous for removing air bubbles.

According to the second needle device of the present invention, the protrusion is provided on the inner hub. Therefore, a liquid flowing out from the opening of the through-hole formed in the inner hub is divided into streams moving on both sides of the protrusion, whereby the flow of the liquid moving in the circumferential direction of the inner hub can be promoted. As a result, the removal of air bubbles in the circumferential direction of the inner hub is promoted. Therefore, according to the present invention, when a liquid is injected into the needle device in the priming operation, air can be reliably replaced with the liquid, whereby air bubbles can be prevented from remaining on the outer circumferential surface of the inner hub.

In the second needle device of the present invention, the inner hub preferably includes a recessed portion at which the outer circumferential surface of the inner hub is recessed inward, and the protrusion preferably protrudes from the recessed portion. With this configuration, the protrusion can be formed while an outer diameter dimension of the inner hub is maintained.

The protrusion is preferably arranged to guide a liquid flowing out from the opening of the through-hole in a circumferential direction of the inner hub.

When the protrusion is viewed from above, a wall surface of the protrusion preferably faces the opening of the through-hole. With this configuration, the flow of the liquid flowing out of the through-hole is limited by the wall surface of the protrusion so that the liquid is divided into streams moving on both sides of the protrusion, whereby the flow of the liquid moving in the circumferential direction of the inner hub is promoted.

The opening of the through-hole preferably is interposed between the recessed portions in a circumferential direction of the inner hub. With this configuration, the recessed portion plays the role of a groove that guides the flow of the liquid in the circumferential direction of the inner hub. Thus, this configuration is advantageous for promoting the flow of the liquid moving in the circumferential direction of the inner hub.

When the inner hub is viewed from above, on a center axis of the inner hub, a dimension of a gap between the protrusion and the opening of the through-hole is preferably smaller than or equal to one half of a shortest distance between the opening of the through-hole and the tip of the inner hub. With this configuration, the liquid more easily moves and spreads from the through-hole of the inner hub in the circumferential direction of the inner hub. Thus, this configuration is more advantageous for removing air bubbles.

When the inner hub is viewed from above, side surfaces on both sides of the protrusion preferably are arranged to form a substantially V-shape, and the width of the protrusion preferably becomes gradually wider toward the through-hole. With this configuration, the protrusion has a sharp tapered tip portion, whereby air bubbles can be prevented from remaining at the tip portion of the protrusion.

The present invention will be described in detail hereinafter with reference to preferred embodiments. Note that the present invention is not intended to be limited to the embodiments described below. The drawings referenced herein schematically show only the main components necessary for description of the present invention, of the components of the embodiments of the present invention, for the sake of convenience. Therefore, the present invention may include suitable components that are not shown in the drawings.

The present invention relates to a needle device. In the embodiments described below, the needle device of the present invention will be described using an example medical indwelling needle device whose needle portion has a double structure including an outer needle and an inner needle. Such an indwelling needle device is used for infusion and blood transfusion. Infusion and blood transfusion are performed while only the soft outer needle is left at an insertion site.

First Embodiment

Figure 2:
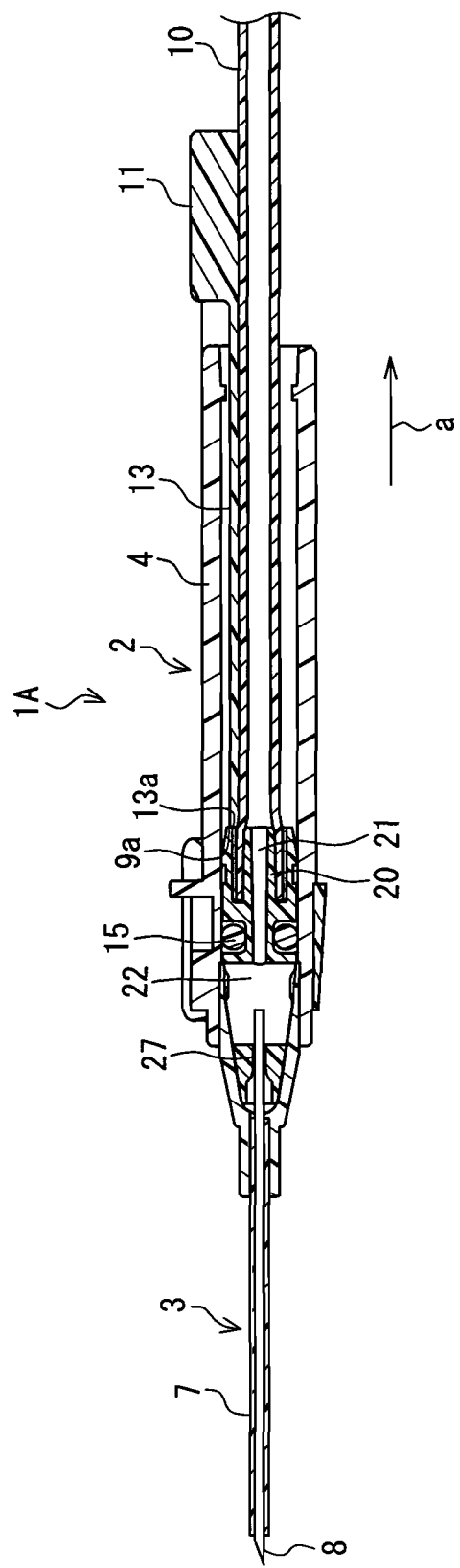
FIG. 2 is a cross-sectional view of the indwelling needle device 1A of FIG. 1 which is taken along a longitudinal direction thereof.
Figure 3:
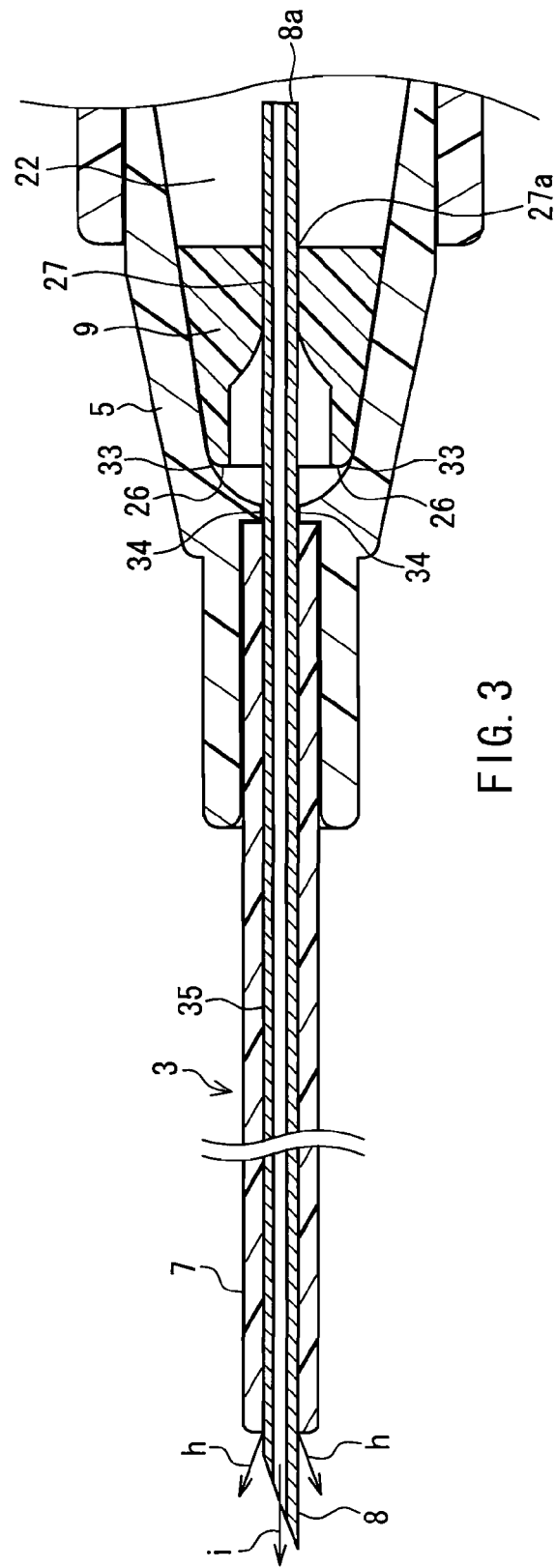
FIG. 3 is an enlarged view of a tip portion of the indwelling needle device 1A of FIG. 2.
Figure 4:
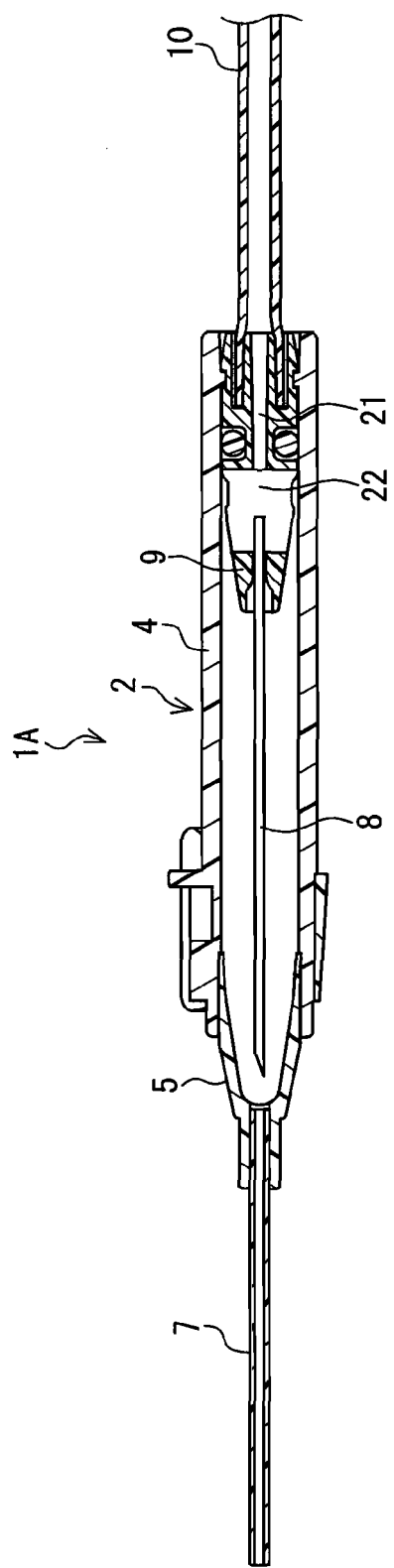
FIG. 4 is a cross-sectional view showing a state in which an inner needle 8, which was in the state of FIG. 2, has been pulled into a shield cylinder 4.

FIG. 1 is a perspective view of an external appearance of an indwelling needle device 1A according to a first embodiment of the present invention. FIG. 2 is a cross-sectional view of the indwelling needle device 1A of FIG. 1 which is taken along a longitudinal direction thereof. FIG. 3 is an enlarged view of a tip portion of the indwelling needle device 1A of FIG. 2. FIG. 4 is a cross-sectional view showing a state in which an inner needle 8, which was in the state of FIG. 2, has been pulled into a shield cylinder 4. Firstly, a basic configuration of the indwelling needle device 1A will be described with reference to FIGS. 1-4.

In FIGS. 1 and 2, the indwelling needle device 1A includes a cylindrical body 2 in which an outer hub 5 is attached to a tip of the shield cylinder 4. The body 2 includes a needle portion 3 (FIG. 2) at a tip portion thereof. In FIG. 1, a cap 6 is attached to the needle portion 3. The shield cylinder 4 and the outer hub 5 are made of for example, polycarbonate, polypropylene, or the like.

As shown in FIG. 3, the needle portion 3 has a double structure in which the hard inner needle 8 made of a metal is inserted in a hollow portion of a tube-like soft outer needle 7. The outer needle 7 is fixed to the outer hub 5, and the inner needle 8 is fixed to an inner hub 9. The inner hub 9 is made of for example, polycarbonate, polypropylene, or the like. The outer needle 7 is made of for example, polyurethane elastomer, fluoroplastic such as polytetrafluoroethylene, or the like.

Figure 6:
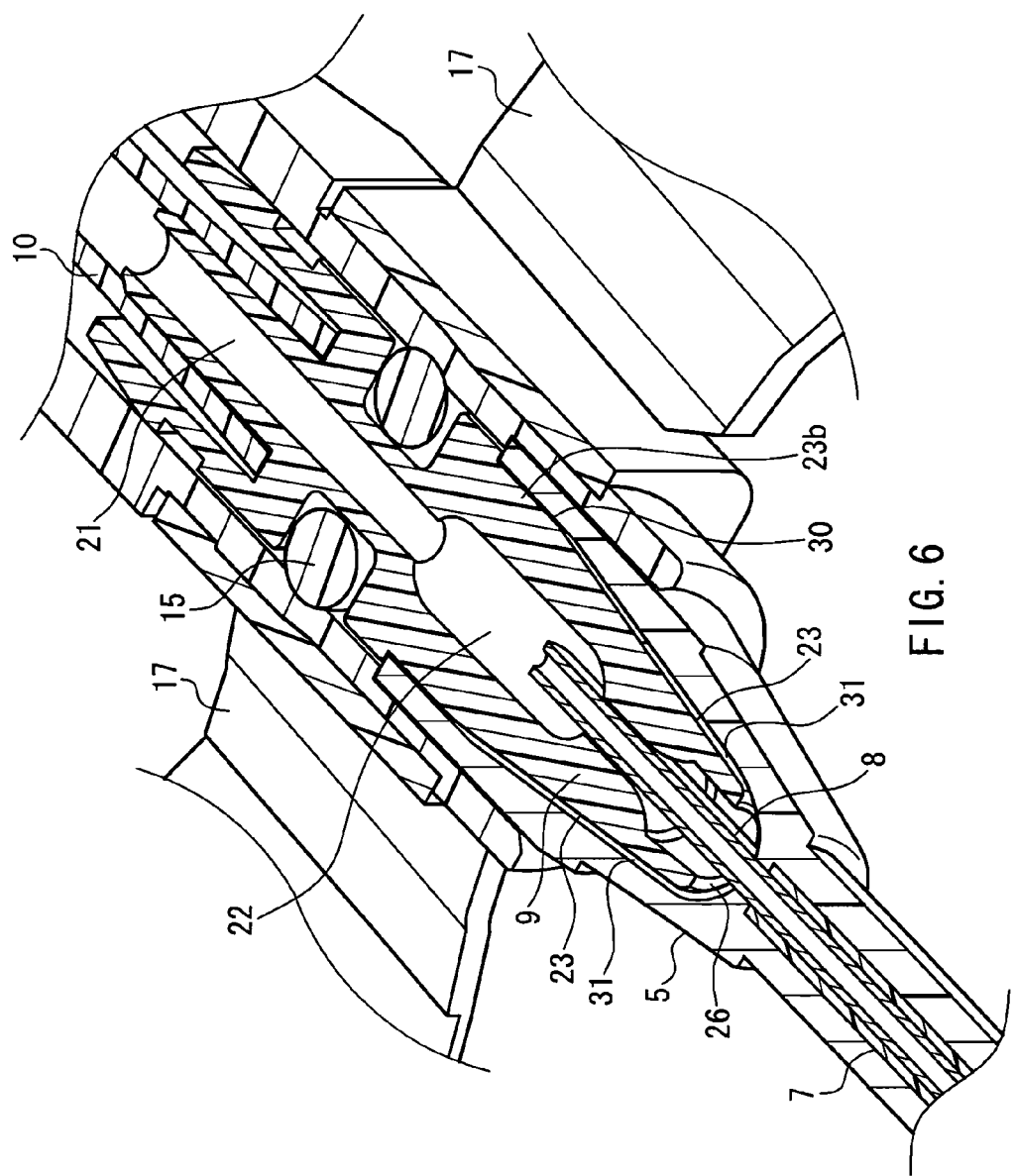
FIG. 6 is an enlarged cross-sectional view of the vicinity of the inner hub 9 according to the first embodiment of the present invention, showing a cross-section of the inner hub 9 which is taken along a radial direction of the through-hole 22.
Figure 7:
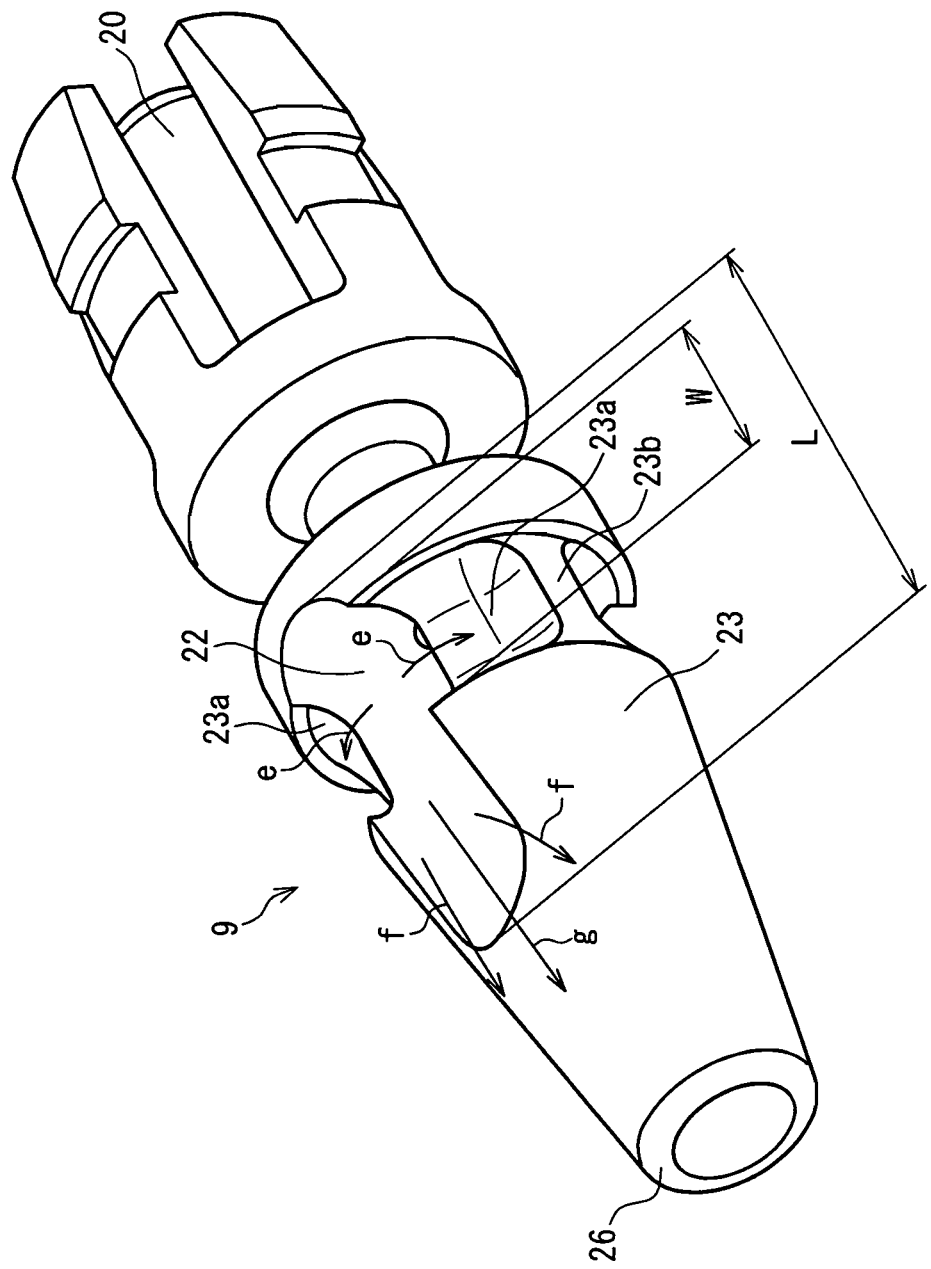
FIG. 7 is an enlarged perspective view of the inner hub 9 according to the first embodiment of the present invention.

In FIG. 3, the inner needle 8 is inserted in a hole 27 of the inner hub 9. By applying an adhesive to an end portion 27a of the hole 27, the inner needle 8 can be fixed to the inner hub 9. The inner needle 8 projects into a through-hole 22. If the amount by which the inner needle 8 protrudes is set to be sufficiently large, even when the projecting amount of the inner needle 8 varies during manufacture, the inner needle 8 is allowed to project into the through-hole 22. For example, as shown in FIGS. 6 and 7 described below, the length of the through-hole 22 in an axial direction of the inner hub 9 is set to be long enough to ensure a sufficient projecting amount of the inner needle 8 into the through-hole 22. As a result, a sufficient distance is ensured between the end portion 27a of the hole 27 and an end portion 8a of the inner needle 8, and therefore, the adhesive is prevented from entering the hollow portion of the inner needle 8 and thereby dogging the inner needle 8. Note that, as in a second embodiment described below, the inner needle 8 may be fixed to the inner hub 9 without causing the inner needle 8 to project into the through-hole 22.

As shown in FIG. 2, the inner hub 9 is housed in the body 2 and can be moved in the shield cylinder 4 in an axial direction of the shield cylinder 4. A sealing O-ring 15 is attached to the inner hub 9. A tube 10 is connected to a pipe-like portion 20 at a rear end of the inner hub 9 (see FIG. 5). By pulling the tube 10 in a direction indicated by an arrow "a," the inner hub 9 is moved in the shield cylinder 4 in the direction indicated by the arrow "a." As a result, the inner needle 8 integrated with the inner hub 9 is pulled into the shield cylinder 4 as shown in FIG. 4.

In FIG. 1, a ring portion 16 is attached to the shield cylinder 4, surrounding an outer circumference of the shield cylinder 4. A pair of wing portions 17 are integrated with the ring portion 16. Moreover, a hub movement limiting member 11 is attached removably to the shield cylinder 4. The hub movement limiting member 11 includes a pair of cantilever portions 12. In FIG. 1, although only one of the pair of cantilever portions 12 is shown, the pair of cantilever portions 12 are provided so as to sandwich the shield cylinder 4.

In the state of FIG. 1, when the pair of wing portions 17 are lifted up and grasped, tip portions 12a of the pair of cantilever portions 12 are grasped while being pressed against the ring portion 16 via the pair of wing portions 17. While the pair of cantilever portions 12 are grasped in this manner, the hub movement limiting member 11 is fixed to the shield cylinder 4.

Moreover, as shown in FIG. 2, a stopper 13 is integrated with the hub movement limiting member 11. In the state of FIG. 2, the stopper 13 is inserted in the shield cylinder 4, and a tip 13a of the stopper 13 abuts a rear end surface 9a of the inner hub 9.

Therefore, when the cantilever portions 12 of the hub movement limiting member 11 are grasped, movement of the inner hub 9, and also the inner needle 8 integrated with the inner hub 9, is limited. Therefore, in this state, the inner needle 8 can be inserted into a patient without being pushed back toward the shield cylinder 4.

When the inner needle 8 is inserted, the soft outer needle 7 is also inserted. After the inner needle 8 and the outer needle 7 are inserted, if the cantilever portions 12 are released and the tube 10 is pulled in the direction indicated by the arrow "a," the inner needle 8 integrated with the inner hub 9 is pulled into the shield cylinder 4 as shown in FIG. 4. As a result, only the soft outer needle 7 is left at the insertion site. Therefore, even when the patient moves, pain at the insertion site can be relieved, and damage to a blood vessel can be avoided.

In the state of FIG. 4, a liquid such as a drug solution etc. to be administered to a patient is supplied from the tube 10 to the inner hub 9. The inner hub 9 includes a flow path 21 extending along the axial direction of the inner hub 9, and the through-hole 22 penetrating the inner hub 9 in a radial direction thereof. The flow path 21 and the through-hole 22 are connected together. The liquid supplied to the inner hub 9 passes through the flow path 21 and the through-hole 22 before flowing out of the inner hub 9. The liquid flowing out of the inner hub 9 passes through the body 2 to reach the hollow portion of the outer needle 7 before being administered to the patient's body.

Here, when a drug solution etc. is administered, if air is present in the indwelling needle device 1A, the air enters a blood vessel along with the drug solution etc. Therefore, prior to insertion, the indwelling needle device 1A is filled with a liquid, such as physiological saline, a nutrient solution, etc. This operation is called priming.

Figure 5:
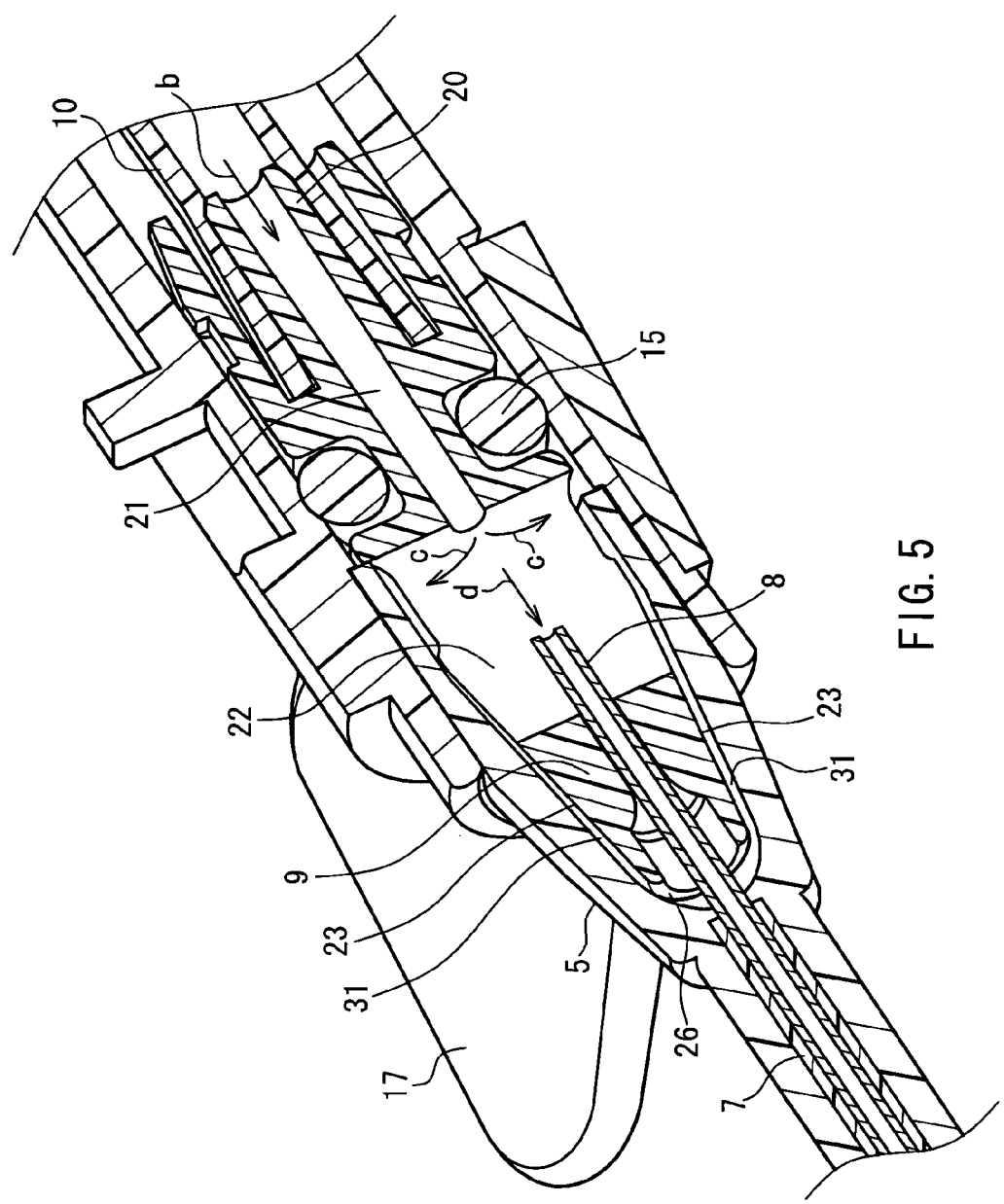
FIG. 5 is an enlarged cross-sectional view of the vicinity of an inner hub 9 according to the first embodiment of the present invention, showing a cross-section of the inner hub 9 which is taken along a penetration direction of a through-hole 22.

The flow of the liquid during the priming operation will be described with reference to FIGS. 5-7. FIG. 5 is an enlarged cross-sectional view of the vicinity of the inner hub 9 in FIG. 2. FIG. 5 shows a cross-section of the inner hub 9 which is taken along a penetration direction of the through-hole 22. FIG. 6 is an enlarged cross-sectional view of the vicinity of the inner hub 9 which is taken along a direction perpendicular to the cross-section direction of FIG. 5. In other words, FIG. 6 shows a cross-section of the inner hub 9 taken along the radial direction of the through-hole 22. FIG. 7 is an enlarged perspective view of the inner hub 9.

The priming operation is performed while the inner needle 8 projects from the outer needle 7 as shown in FIG. 2. In FIG. 5, during the priming operation, a liquid such as physiological saline etc. is supplied from the tube 10 toward the inner hub 9 (in a direction indicated by an arrow "b"). The liquid supplied to the inner hub 9 passes through the flow path 21 to flow into the through-hole 22. A portion of the liquid flowing into the through-hole 22 flows toward the outer circumferential surface of the inner hub 9, i.e., openings at both ends of the through-hole 22 (in directions indicated by arrows "c"). Another portion of the liquid flowing into the through-hole 22 flows toward the inside of the inner needle 8 (in a direction indicated by an arrow "d").

The liquid flowing in the directions indicated by the arrows "c" passes through a gap between the outer circumferential surface of the inner hub 9 and an inner circumferential surface of the outer hub 5 to flow toward a tip 26 of the inner hub 9. Before describing the flow of the liquid flowing out from the openings at both ends of the through-hole 22, a configuration of the inner hub 9 and a relationship between the inner hub 9 and the outer hub 5 will be described.

FIG. 7 is an enlarged perspective view of the inner hub 9. Recessed portions 23a in which the outer circumferential surface 23 of the inner hub 9 is recessed inward are formed in the outer circumferential surface 23. The recessed portions 23a are connected to the openings of the through-hole 22. In the example of FIG. 7, the through-hole 22 is interposed between the recessed portions 23a in a circumferential direction of the inner hub 9. The recessed portions 23a are separated by separator surfaces 23b serving as boundaries.

Note that FIG. 7 shows a portion of the outer circumferential surface of the inner hub 9. Similar to FIG. 7, recessed portions 23a are formed on a side (on the back side of the drawing sheet) on which the other opening of the through-hole 22 is provided, with the through-hole 22 being interposed between the recessed portions 23a in the circumferential direction of the inner hub 9. The recessed portions 23a connected to one opening of the through-hole 22 and the recessed portions 23a connected to the other opening of the through-hole 22 are separated from each other by a pair of the separator surfaces 23b. Therefore, the recessed portions 23 are not continuous in the circumferential direction.

The flow of a liquid flowing out of the through-hole 22 will be described specifically hereinafter. Arrows "e," "f" and "g" of FIG. 7 indicate directions of the flow of the liquid flowing out of the through-hole 22. As shown in FIG. 7, both sides of the opening of the through-hole 22 in the circumferential direction of the inner hub 9 are connected to the pair of recessed portions 23a. At a portion in which the recessed portion 23a is formed, the flow of the liquid is guided by the recessed portion 23a.

Therefore, a part of the liquid flowing out of the through-hole 22 is limited so that the part of the liquid flows along the recessed portions 23a. Therefore, flows (arrows "e") moving in the circumferential direction of the inner hub 9 occur on both sides of the through-hole 22.

As described above, the recessed portions 23a are separated from each other by the separator surfaces 23b serving as boundaries. The depth of the recessed portion 23a becomes gradually shallower in a direction from the opening of the through-hole 22 to the separator surface 23b. The separator surface 23b is closer to the inner circumferential surface of the outer hub 5 than the recessed portion 23a is, but is not in complete contact therewith (see FIG. 6). Therefore, a gap 30 is formed between the separator surface 23b and the inner circumferential surface of the outer hub 5. Therefore, the liquid flow indicated by the arrow "e" of FIG. 7 moves up onto the separator surface 23b. After reaching the separator surface 23b, the liquid flows in the gap 30 toward the tip 26 of the inner hub 9.

FIGS. 5 and 6 show the outer circumferential surface 23 of the inner hub 9 in a portion in which the recessed portion 23a is not formed. The outer circumferential surface 23 of the inner hub 9 shown in FIGS. 5 and 6 is close to the inner circumferential surface of the outer hub 5, but is not in complete contact therewith. Therefore, a gap 31 is formed between the outer circumferential surface 23 of the inner hub 9 and the inner circumferential surface of the outer hub 5. Therefore, the liquid indicated by the arrows "f" and "g" of FIG. 7 flows in the gap 31 (FIGS. 5 and 6) toward the tip 26 of the inner hub 9.

In other words, the liquid flowing out of the through-hole 22 generally moves in the axial direction of the inner hub 9 toward the tip 26 of the inner hub 9. However, the recessed portion 23a limits the flow of the liquid, and therefore, the flow of the liquid moving along the circumferential direction of the inner hub 9 also is promoted.

In FIG. 3, the liquid which has reached the tip 26 of the inner hub 9 further moves toward the inside of the outer needle 7. The vicinity of the tip 26 of the inner hub 9 is not in complete contact with the inner circumferential surface of the outer hub 5, and therefore, a gap 33 is formed therebetween. A gap 34 is also formed between the hole of the outer hub 5 and the inner needle 8. A gap 35 is also formed between the inner circumferential surface of the outer needle 7 and the outer circumferential surface of the inner needle 8.

Therefore, the liquid flowing in the gap 31 toward the tip 26 of the inner hub 9 passes through the gap 33, the gap 34, and the gap 35 and then flows out from the tip of the outer needle 7 (an arrow "h"). On the other hand, the liquid moving in the direction indicated by the arrow "d" of FIG. 5 passes through the hollow portion of the inner needle 8 and then flows out from the tip of the inner needle 8 as indicated by an arrow "i" of FIG. 3.

Therefore, by performing the above priming operation on the indwelling needle device 1A, the space and the gaps located between the through-hole 22 and the tips of the inner needle 8 and the outer needle 7 are filled with the liquid, i.e., air is removed from the space and the gaps.

Figure 8:
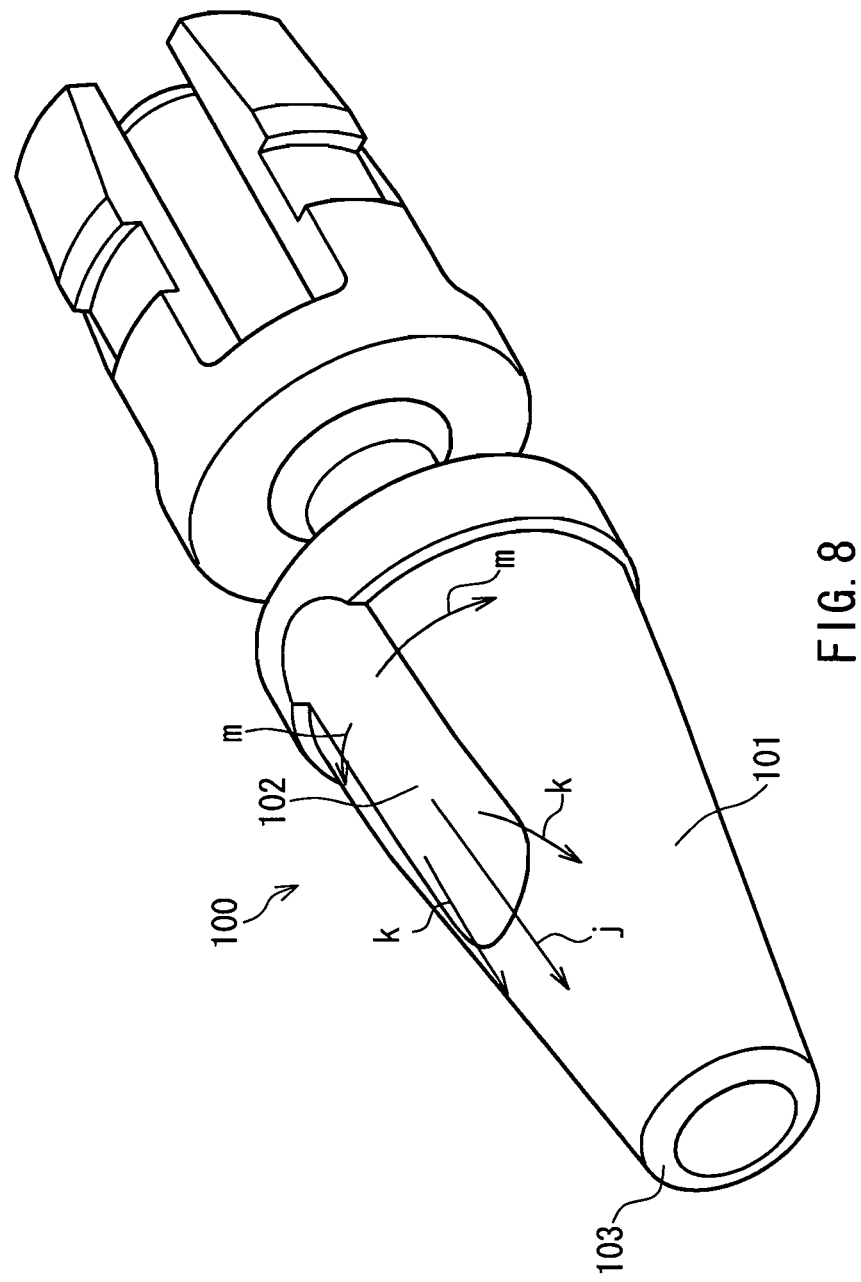
FIG. 8 is an enlarged perspective view of an inner hub 100 according to a comparative example.

Next, the inner hub 9 of the first embodiment will be described by comparing it with a comparative example. FIG. 8 is a perspective view of an inner hub 100 according to the comparative example. A through-hole 102 is formed in an even outer circumferential surface 101 of the inner hub 100, penetrating therethrough in a radial direction. Unlike the inner hub 9 of FIG. 7, the recessed portion 23a is not formed in the outer circumferential surface 101 of the inner hub 100.

In the inner hub 100 of FIG. 8, a liquid from the through-hole 102 flows toward a tip 103 of the inner hub 100. Therefore, the liquid moving toward the tip 103 of the inner hub 100 forms a strong flow (arrows "j" and "k"), and air is discharged easily along with this flow.

In contrast to this, a flow (an arrow "m") in a circumferential direction of the inner hub 100 is weak. Therefore, it gradually becomes more difficult for the liquid to reach a portion which is located farther away from the opening of the through-hole 102 in the circumferential direction of the inner hub 100. Therefore, air bubbles are more likely to remain at a portion located farther away from the opening of the through-hole 102 in the circumferential direction of the inner hub 100.

In the first embodiment, as described above, as shown in FIG. 7, the formation of the recessed portion 23a allows the liquid flowing out from the opening of the through-hole 22 to divide into streams moving on both sides in the circumferential direction of the through-hole 22, whereby the flow moving in the circumferential direction of the inner hub 9 can be promoted. Therefore, the removal of air bubbles is promoted even in a portion distant from the opening of the through-hole 22 in the circumferential direction of the inner hub 9.

As described above, the depth of the recessed portion 23a becomes gradually shallower in a direction from the opening of the through-hole 22 to the separator surface 23b. Therefore, it is more likely that air bubbles move up onto the separator surface 23b along with the flow of the liquid, and then flow toward the tip 26 of the inner hub 9. This is also advantageous for promoting the removal of air bubbles.

Note that the entirety or a portion of the recessed portion 23a may become gradually shallower toward the separator surface 23b. For example, the depth of the recessed portion 23a may be constant in a region extending from the opening of the through-hole 22 to some point in the circumferential direction, and may become gradually shallower toward the separator surface 23b in a region extending from this point to the separator surface 23b.

Therefore, according to this embodiment, air reliably can be replaced with the liquid by loading the liquid using the priming operation, whereby air bubbles can be prevented from remaining on the outer circumferential surface of the inner hub 9.

According to the inventors' experimental studies, the air bubbles remaining tend to occur selectively at a specific portion, rather than on the entire outer circumferential surface of the inner hub 9. Therefore, in order to achieve removal of air bubbles, it is effective to avoid an excessively large recessed portion 23a so that the flow of the liquid is concentrated into a portion in which air bubbles are likely to remain. Specifically, as shown in FIG. 7, a width W of the recessed portion 23a in the axial direction of the inner hub 9 is preferably smaller than or equal to one half of a length L of the opening of the through-hole 22. This holds true in the examples of FIGS. 9-11 described below.

Other examples will be described hereinafter with reference to FIGS. 9-11. Components which are the same as or similar to those of the above example are indicated by the same reference characters and will not be described. While FIGS. 9-11 show a side on which one of the openings of the through-hole 22 is provided, a shape similar to that of FIGS. 9-11 is provided on a side on which the other opening of the through-hole 22 is provided.

Figure 9:
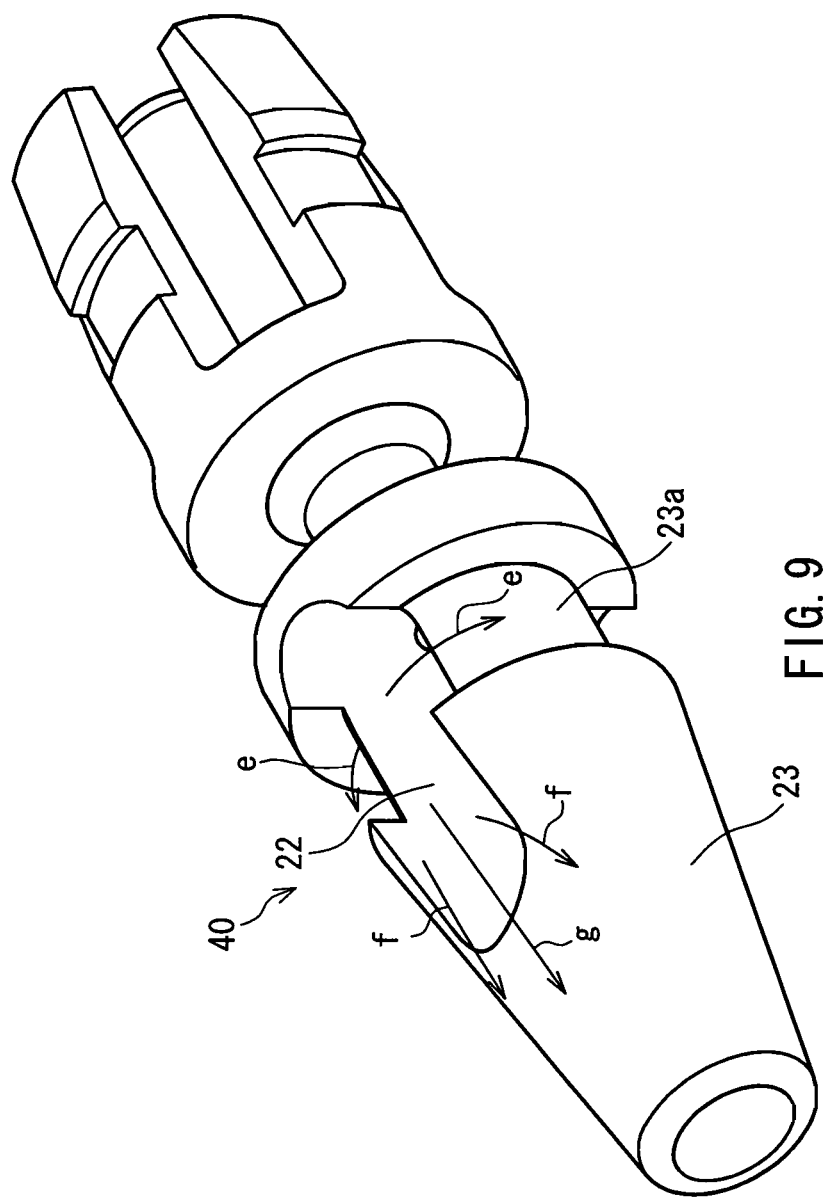
FIG. 9 is an enlarged perspective view of an inner hub 40 according to a second example of the first embodiment of the present invention.

FIG. 9 is an enlarged perspective view of an inner hub 40 according to a second example of the first embodiment. While the recessed portions 23a are separated from each other in the circumferential direction by the separator surfaces 23b serving as boundaries in the inner hub 9 of FIG. 7, a recessed portion 23a is formed over the entire circumference of the inner hub 40 of FIG. 9 except for a portion in which the through-hole 22 is formed.

With this configuration, similar to the example of FIG. 7, a liquid flows toward the tip 26 of the inner hub 40 as indicated by arrows "l" and "g." Moreover, with this configuration, similar to the example of FIG. 7, a flow (an arrow "e") of the liquid moving along the recessed portion 23a in the circumferential direction of the inner hub 40 can be promoted, whereby the removal of air bubbles can be promoted.

Figure 10:
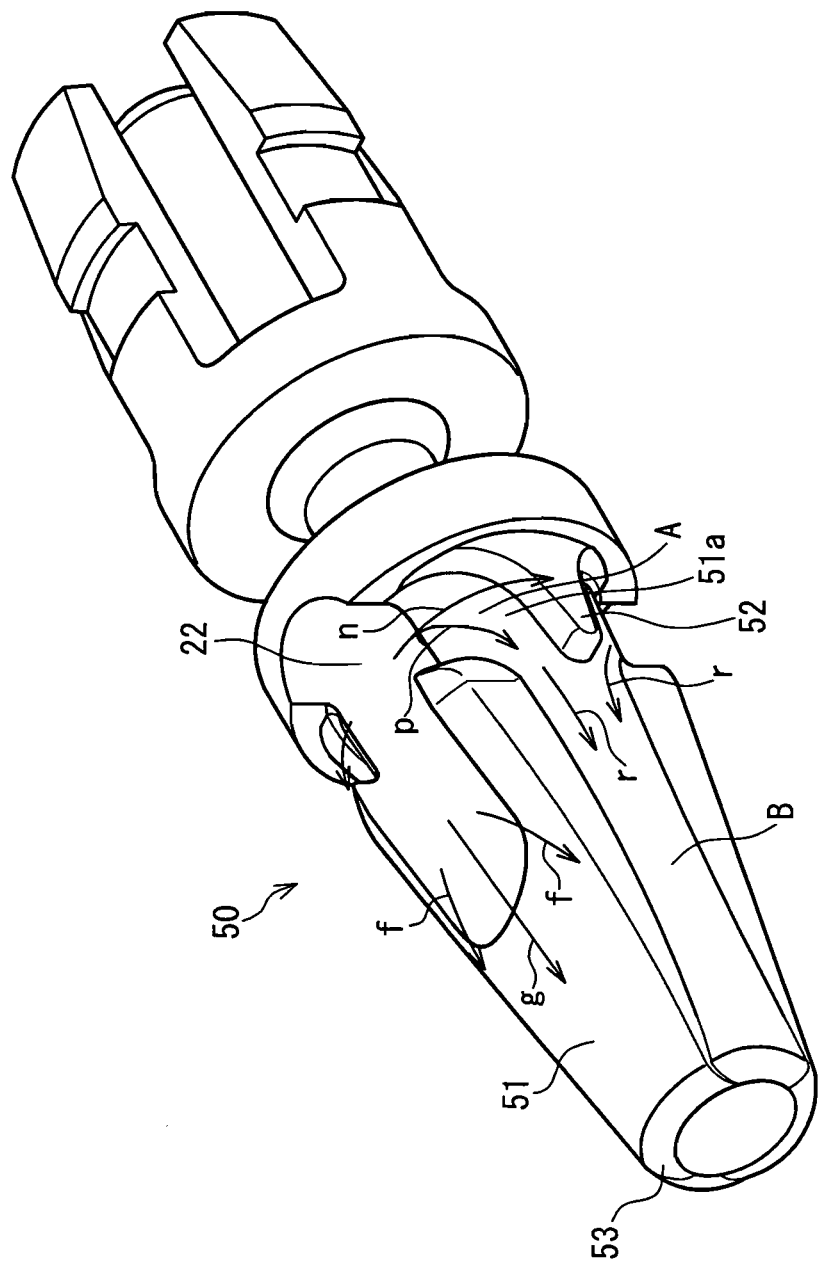
FIG. 10 is an enlarged perspective view of an inner hub 50 according to a third example of the first embodiment of the present invention.
Figure 11:
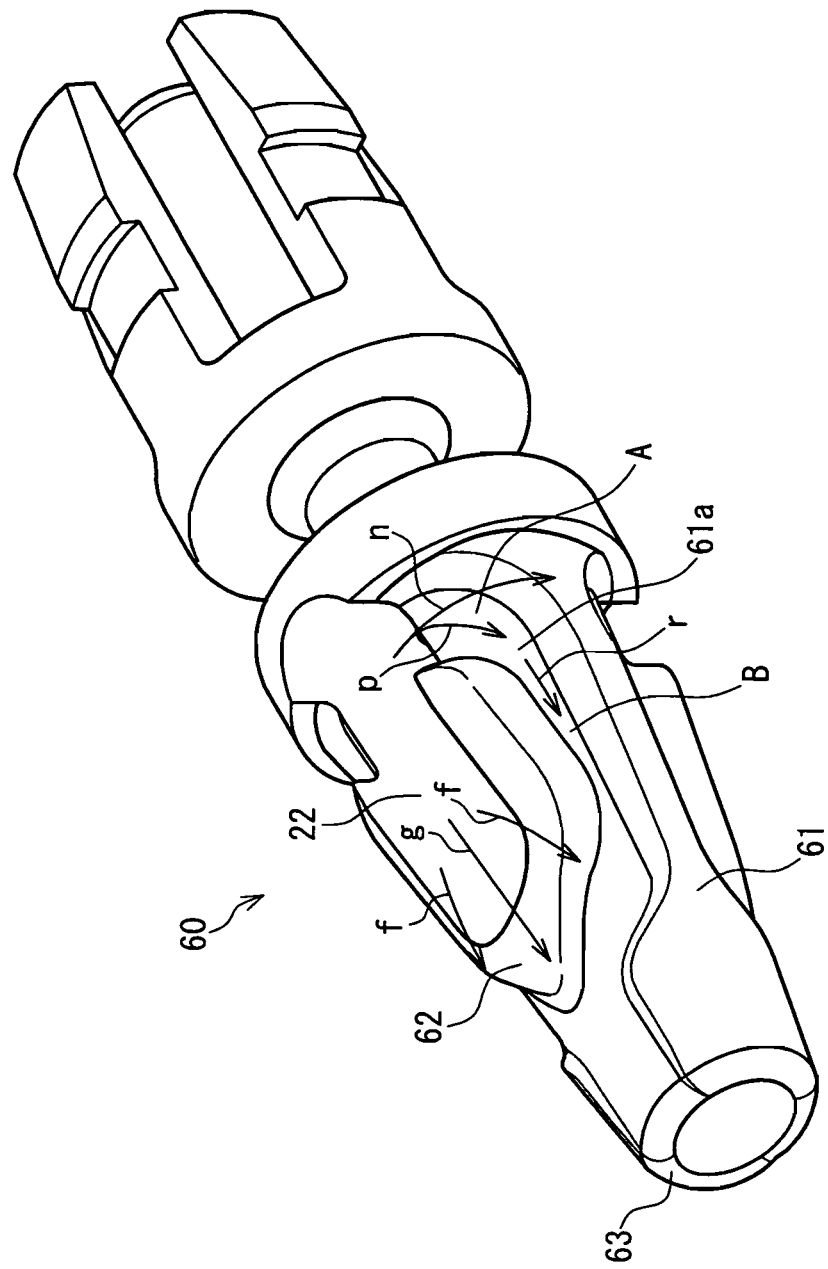
FIG. 11 is an enlarged perspective view of an inner hub 60 according to a fourth example of the first embodiment of the present invention.

FIG. 10 is an enlarged perspective view of an inner hub 50 according to a third example of the first embodiment. A recessed portion 51a at which an outer circumferential surface 51 of the inner hub 50 is recessed inward is formed in the outer circumferential surface 51. The example of FIG. 10 is different from the examples of FIGS. 7 and 9 in that the recessed portion 51a of the inner hub 50 includes a portion B extending in an axial direction of the inner hub 50.

A portion of the recessed portion 51a is divided by a protrusion 52 which protrudes from a bottom surface of the recessed portion 51a. A portion A of the recessed portion 51a separated by the protrusion 52 is connected to the through-hole 22 in the circumferential direction. A portion (the portion B) of the recessed portion 51a which is closer to a tip 53 of the inner hub 50 than the portion A is, is formed to extend in the axial direction of the inner hub 50.

In the example of FIG. 10, similar to the example of FIG. 7, a liquid flows toward the tip 53 of the inner hub 50 as indicated by arrows "f" and "g." At the portion A of the recessed portion 51a, flows (arrows "n" and "p") moving in the circumferential direction of the inner hub 50 occur. A top surface of the protrusion 52 is not in complete contact with the inner circumferential surface of the outer hub 5 (FIG. 5), i.e., a gap is formed therebetween. Therefore, a part (the arrow "n") of the flow in the circumferential direction moves over the protrusion 52 and then moves further in the circumferential direction.

Therefore, with the configuration of FIG. 10, the flows (the arrows "n" and "p") moving along the recessed portion 51a in the circumferential direction of the inner hub 50 are promoted, and a flow (an arrow "r") moving in the axial direction of the inner hub 50 also is promoted. Therefore, the configuration of FIG. 10 is also advantageous for promoting the removal of air bubbles in the axial direction of the inner hub 50.

FIG. 11 is an enlarged perspective view of an inner hub 60 according to a fourth example of the first embodiment. A recessed portion 61a at which an outer circumferential surface 61 of the inner hub 60 is recessed inward is formed in the outer circumferential surface 61. The example of FIG. 11 is different from the examples of FIGS. 7 and 9 in that the recessed portion 61a of the inner hub 60 includes a portion B extending in an axial direction of the inner hub 60.

An opening of the through-hole 22 is surrounded by a protrusion 62, except for a portion in which the recessed portion 61a is formed. A portion A of the recessed portion 61a is connected to the through-hole 22 in the circumferential direction. A portion (a portion B) of the recessed portion 61a which is closer to a tip 63 of the inner hub 60 than the portion A is, is formed to extend in the axial direction of the inner hub 60.

In the example of FIG. 11, similar to the example of FIG. 7, a liquid flows toward the tip 63 of the inner hub 60 as indicated by arrows "f" and "g." At the portion A of the recessed portion 61a, flows (arrows "n" and "p") moving in the circumferential direction of the inner hub 60 occur. The outer circumferential surface 61 of the inner hub 60 in which the recessed portion 61a is not formed is not in complete contact with the inner circumferential surface of the outer hub 5 (FIG. 5), i.e., a gap is formed therebetween. Therefore, a part (the arrow "n") of the flow in the circumferential direction moves over the outer circumferential surface 61 and then moves further in the circumferential direction.

Therefore, with the configuration of FIG. 11, similar to the configuration of FIG. 10, the flows (the arrows "n" and "p") moving along the recessed portion 61a in the circumferential direction of the inner hub 60 are promoted, and a flow (an arrow "r") moving in the axial direction of the inner hub 60 is also promoted. Therefore, the configuration of FIG. 11 is also advantageous for promoting the removal of air bubbles in the axial direction of the inner hub 60.

Various example inner hubs have been described above. The shape of the inner hub is not limited to the above examples. The inner hub may have any shape as long as the opening of the through-hole and the recessed portion are connected together in the circumferential direction, and the recessed portion can guide a liquid flowing out from the opening of the through-hole in the circumferential direction of the inner hub.

Second Embodiment

Figure 12:
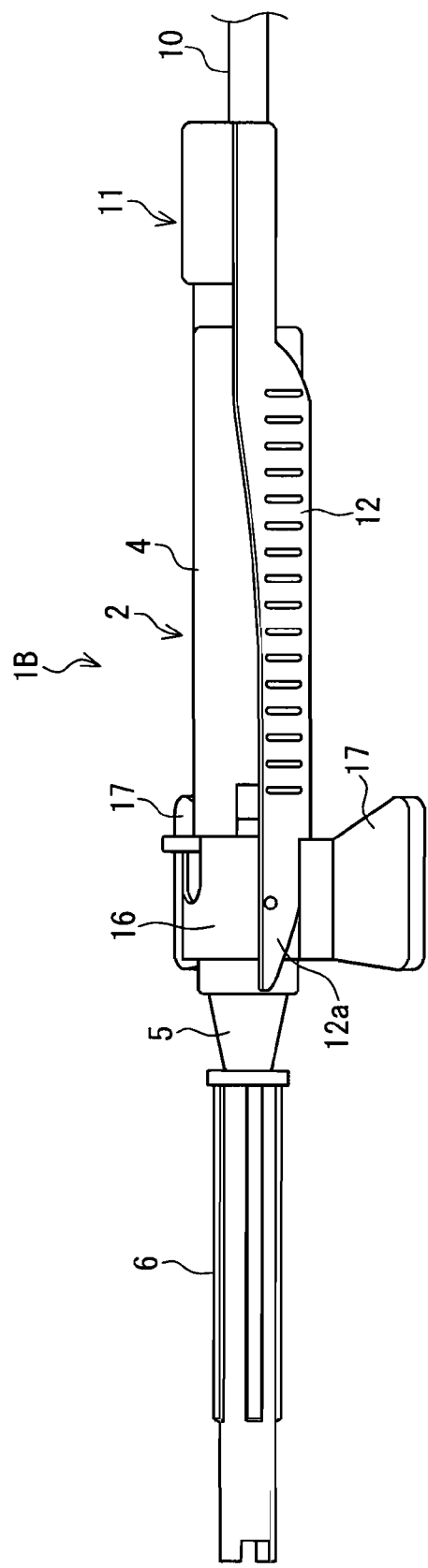
FIG. 12 is a perspective view showing the external appearance of an indwelling needle device 1B according to a second embodiment of the present invention.
Figure 13:
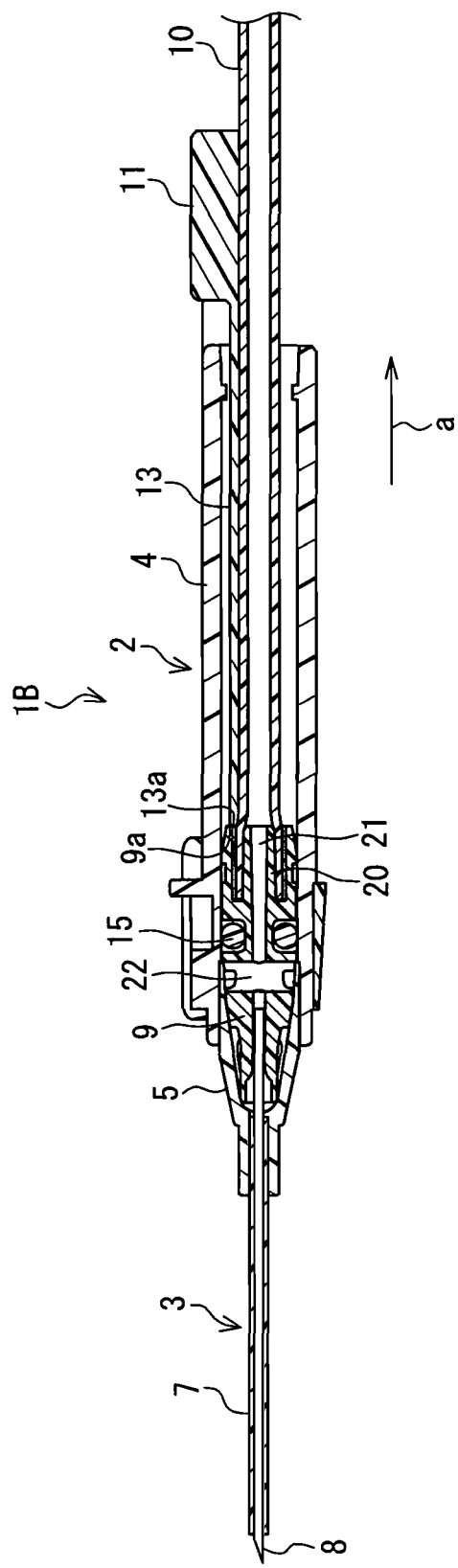
FIG. 13 is a cross-sectional view of the indwelling needle device 1B of FIG. 12 which is taken along a longitudinal direction thereof.
Figure 14:
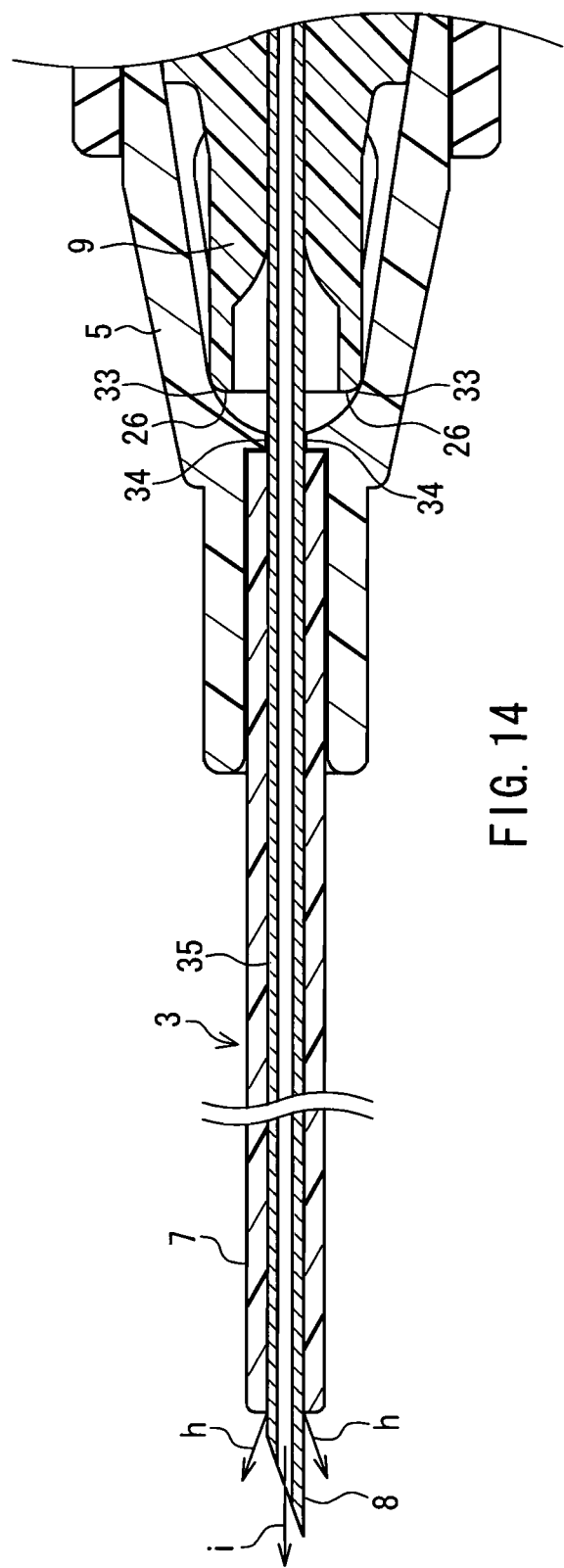
FIG. 14 is an enlarged view of a tip portion of the indwelling needle device 1B of FIG. 13.
Figure 15:
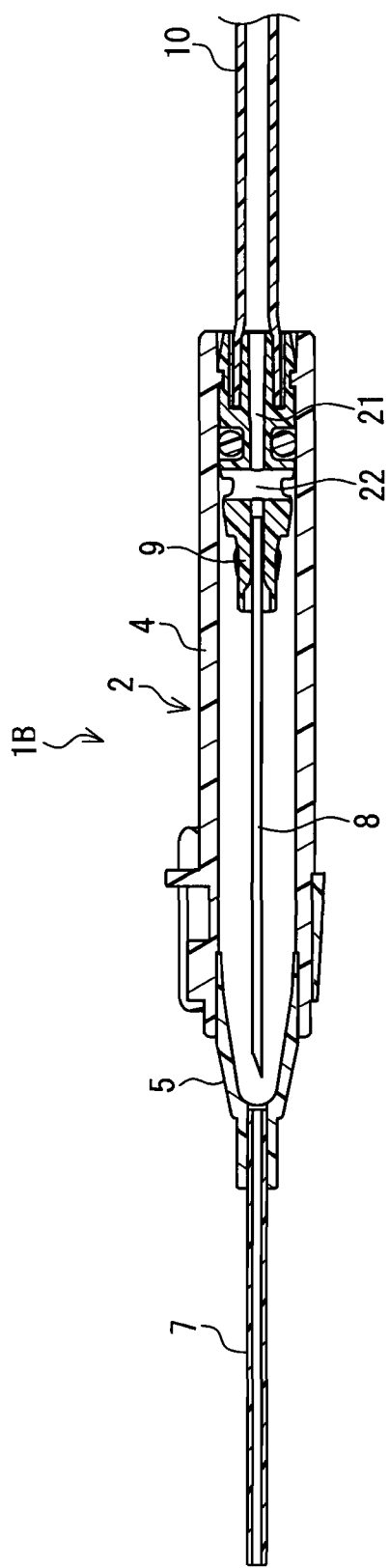
FIG. 15 is a cross-sectional view showing a state in which an inner needle 8, which was in the state of FIG. 13, has been pulled into a shield cylinder 4.

FIG. 12 is a perspective view showing an external appearance of an indwelling needle device 1B according to a second embodiment of the present invention. FIG. 13 is a cross-sectional view of the indwelling needle device 1B of FIG. 12 which is taken along a longitudinal direction thereof. FIG. 14 is an enlarged view of a tip portion of the indwelling needle device 1B of FIG. 13. FIG. 15 is a cross-sectional view showing a state in which an inner needle 8, which was in the state of FIG. 13, has been pulled into a shield cylinder 4. Firstly, a basic configuration of the indwelling needle device 1B will be described with reference to FIGS. 12-15.

In FIGS. 12 and 13, the indwelling needle device 1B includes a cylindrical body 2 in which an outer hub 5 is attached to a tip of the shield cylinder 4. The body 2 includes a needle portion 3 (FIG. 13) at a tip portion thereof. In FIG. 12, a cap 6 is attached to the needle portion 3. The shield cylinder 4 and the outer hub 5 are made of, for example, polycarbonate, polypropylene, or the like.

As shown in FIG. 14, the needle portion 3 has a double structure in which the hard inner needle 8 made of a metal is inserted into a hollow portion of a tube-like soft outer needle 7. The outer needle 7 is fixed to the outer hub 5, and the inner needle 8 is fixed to an inner hub 9. The inner hub 9 is made of, for example, polycarbonate, polypropylene, or the like. The outer needle 7 is made of, for example, polyurethane elastomer, fluoroplastic such as polytetrafluoroethylene, or the like.

In the second embodiment, the inner needle 8 does not project into a through-hole 22. Alternatively, similar to the first embodiment, the inner needle 8 may be fixed to the inner hub 9 so as to project into the through-hole 22.

As shown in FIG. 13, the inner hub 9 is housed in the body 2, and can be moved in the shield cylinder 4 in an axial direction of the shield cylinder 4. A sealing O-ring 15 is attached to the inner hub 9. A tube 10 is connected to a pipe-like portion 20 at a rear end of the inner hub 9 (see FIG. 16). By pulling the tube 10 in a direction indicated by an arrow "a," the inner hub 9 is moved in the shield cylinder 4 in the direction indicated by the arrow "a." As a result, the inner needle 8 integrated with the inner hub 9 is pulled into the shield cylinder 4 as shown in FIG. 15.

In FIG. 12, a ring portion 16 is attached to the shield cylinder 4, surrounding an outer circumference of the shield cylinder 4. A pair of wing portions 17 are integrated with the ring portion 16. Moreover, a hub movement limiting member 11 is attached removably to the shield cylinder 4. The hub movement limiting member 11 includes a pair of cantilever portions 12. In FIG. 12, although only one of the pair of cantilever portions 12 is shown, the pair of cantilever portions 12 are provided so as to sandwich the shield cylinder 4.

In the state of FIG. 12, when the pair of wing portions 17 are lifted up and grasped, tip portions 12a of the pair of cantilever portions 12 are grasped while being pressed against the ring portion 16 via the pair of wing portions 17. While the pair of cantilever portions 12 are grasped in this manner, the hub movement limiting member 11 is fixed to the shield cylinder 4.

Moreover, as shown in FIG. 13, a stopper 13 is integrated with the hub movement limiting member 11. In the state of FIG. 13, the stopper 13 is inserted in the shield cylinder 4, and a tip 13a of the stopper 13 abuts a rear end surface 9a of the inner hub 9.

Therefore, when the cantilever portions 12 of the hub movement limiting member 11 are grasped, movement of the inner hub 9, and also the inner needle 8 integrated with the inner hub 9, is limited. Therefore, in this state, the inner needle 8 can be inserted into a patient without being pushed back toward the shield cylinder 4.

When the inner needle 8 is inserted, the soft outer needle 7 is also inserted. After the inner needle 8 and the outer needle 7 are inserted, if the cantilever portions 12 are released and the tube 10 is pulled in the direction indicated by the arrow "a," the inner needle 8 integrated with the inner hub 9 is pulled into the shield cylinder 4 as shown in FIG. 15. As a result, only the soft outer needle 7 is left at the insertion site. Therefore, even when the patient moves, pain at the insertion site can be relieved and damage to a blood vessel can be avoided.

In the state of FIG. 15, a liquid such as a drug solution etc. to be administered to a patient is supplied from the tube 10 to the inner hub 9. The inner hub 9 includes a flow path 21 extending along the axial direction of the inner hub 9, and the through-hole 22 penetrating the inner hub 9 in a radial direction thereof. The flow path 21 and the through-hole 22 are connected together. The liquid supplied to the inner hub 9 passes through the flow path 21 and the through-hole 22 to flow out of the inner hub 9. The liquid flowing out of the inner hub 9 passes through the body 2 to reach the hollow portion of the outer needle 7 before being administered to the patient's body.

Here, when a drug solution etc. is administered, if air is present in the indwelling needle device 1B, the air enters a blood vessel along with the drug solution etc. Therefore, prior to insertion, the indwelling needle device 1B is filled with a liquid, such as a physiological saline, a nutrient solution, etc. This operation is called priming.

Figure 16:
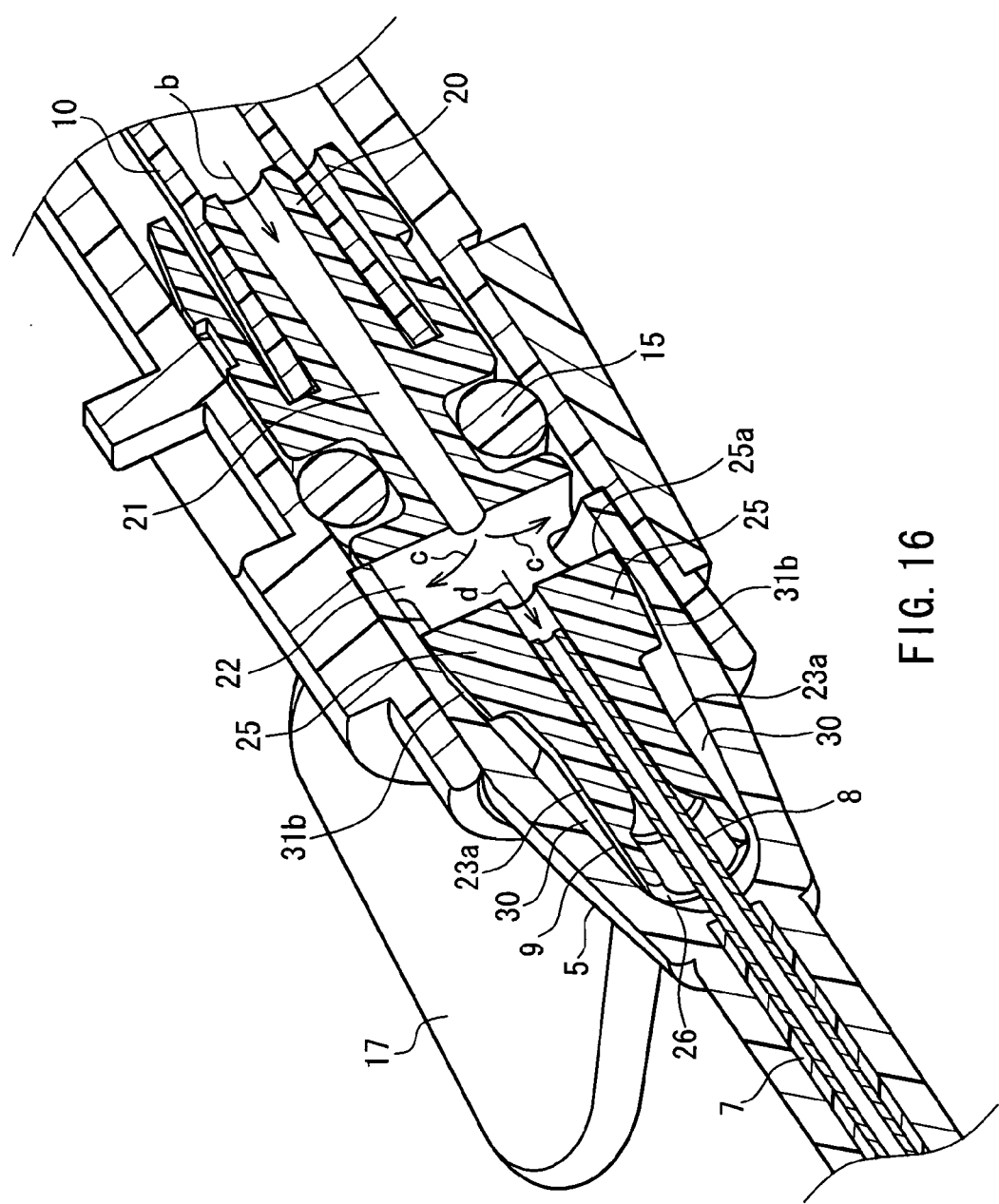
FIG. 16 is an enlarged cross-sectional view of the vicinity of an inner hub 9 according to the second embodiment of the present invention, showing a cross-section of the inner hub 9 which is taken along a penetration direction of a through-hole 22.
Figure 17:
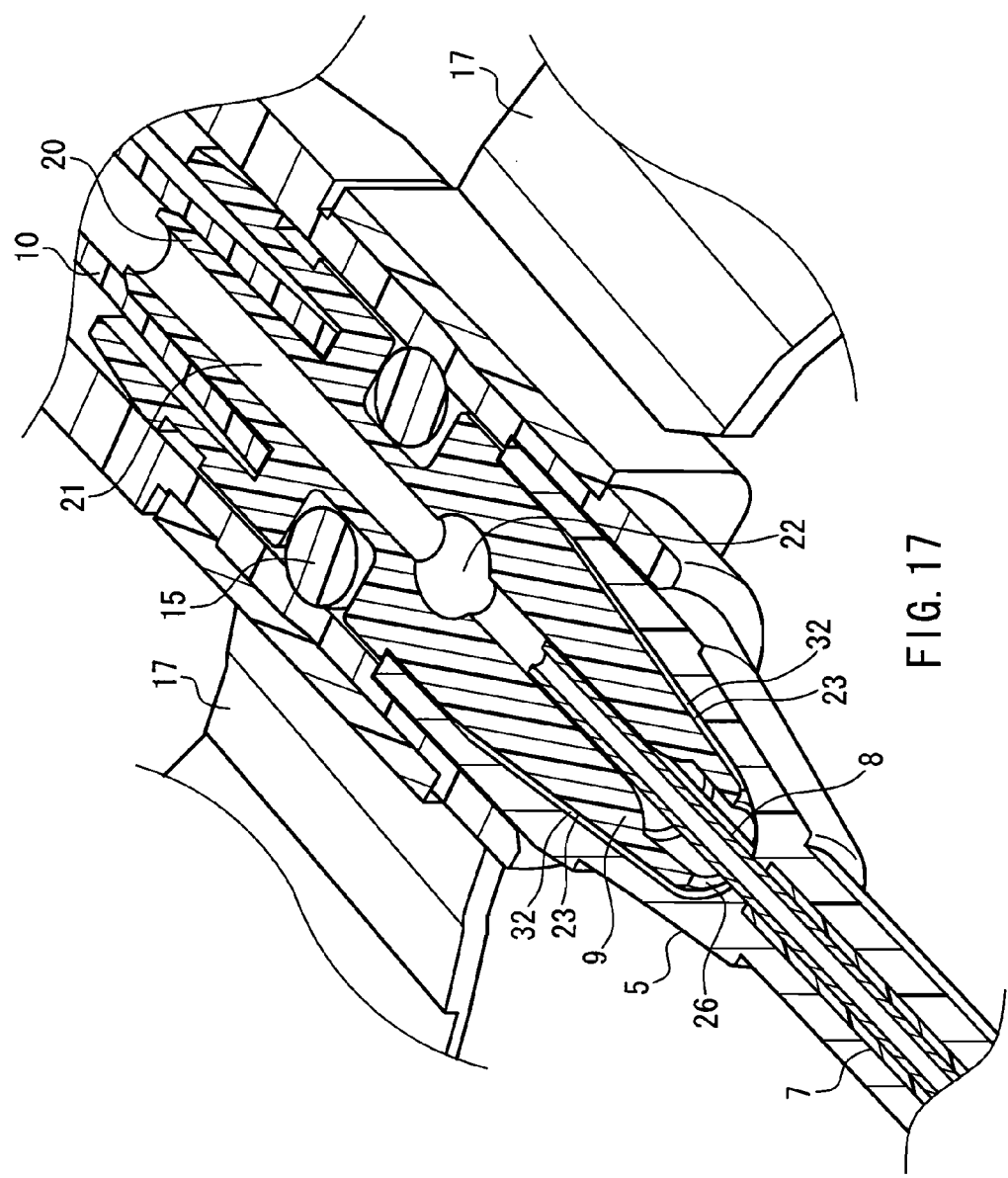
FIG. 17 is an enlarged cross-sectional view of the vicinity of the inner hub 9 according to the second embodiment of the present invention, showing a cross-section of the inner hub 9 which is taken along a radial direction of the through-hole 22.
Figure 18:
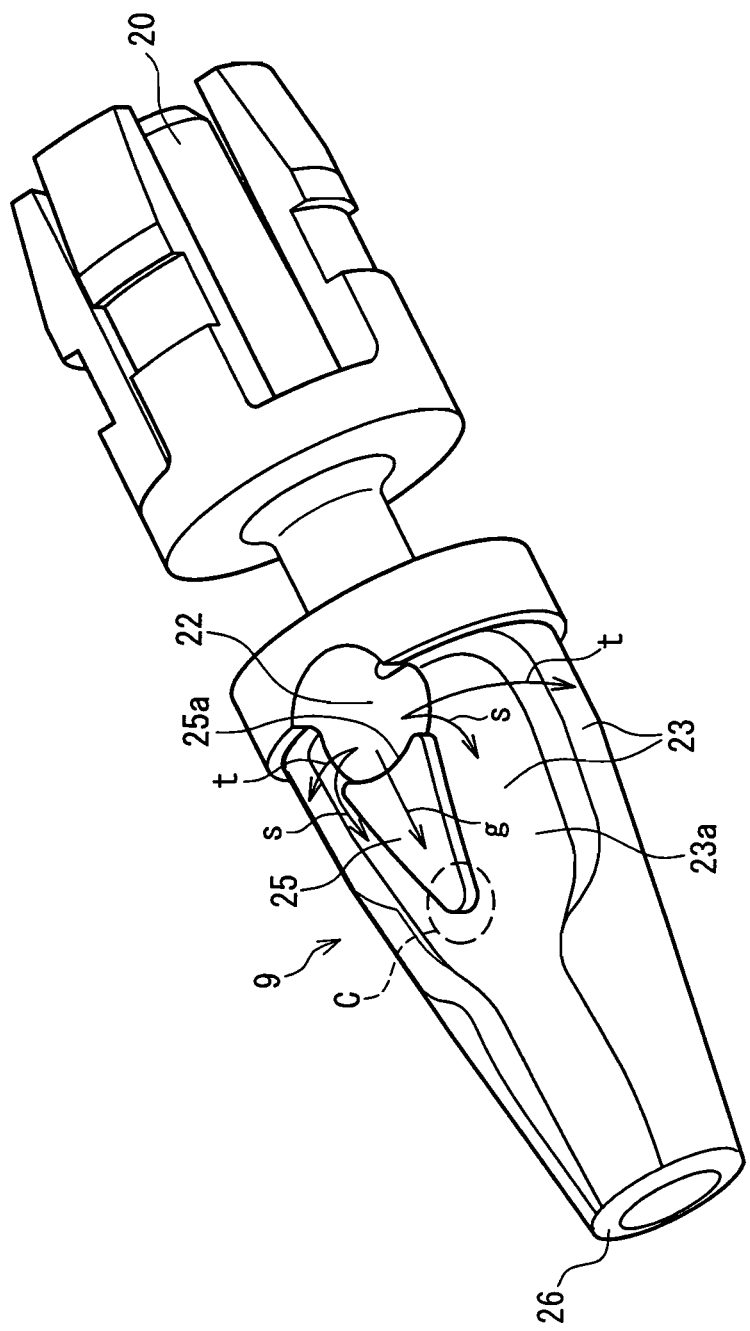
FIG. 18 is an enlarged perspective view of the inner hub 9 according to the second embodiment of the present invention.

The flow of the liquid during the priming operation will be described with reference to FIGS. 16-18. FIG. 16 is an enlarged cross-sectional view of the vicinity of the inner hub 9 in FIG. 13. FIG. 16 shows a cross-section of the inner hub 9 which is taken along a penetration direction of the through-hole 22. FIG. 17 is an enlarged cross-sectional view of the vicinity of the inner hub 9 which is taken along a direction perpendicular to the cross-section direction of FIG. 16. In other words, FIG. 17 shows a cross-section of the inner hub 9 taken along the radial direction of the through-hole 22. FIG. 18 is an enlarged perspective view of the inner hub 9.

The priming operation is performed while the inner needle 8 projects from the outer needle 7 as shown in FIG. 13. In FIG. 16, during the priming operation, a liquid such as physiological saline etc. is supplied from the tube 10 toward the inner hub 9 (in a direction indicated by an arrow "b"). The liquid supplied to the inner hub 9 passes through the flow path 21 to flow into the through-hole 22. A portion of the liquid flowing into the through-hole 22 flows toward the outer circumferential surface of the inner hub 9, i.e., openings at both ends of the through-hole 22 (in directions indicated by arrows "c"). Another portion of the liquid flowing into the through-hole 22 flows toward the inside of the inner needle 8 (in a direction indicated by an arrow "d").

The liquid flowing in the directions indicated by the arrows "c" passes through a gap between the outer circumferential surface of the inner hub 9 and an inner circumferential surface of the outer hub 5 to flow toward a tip 26 of the inner hub 9. Before describing the flow of the liquid flowing out from the openings at both ends of the through-hole 22, a configuration of the inner hub 9 and a relationship between the inner hub 9 and the outer hub 5 will be described.

FIG. 18 is an enlarged perspective view of the inner hub 9. A recessed portion 23a in which the outer circumferential surface 23 of the inner hub 9 is recessed inward is formed in the outer circumferential surface 23. The outer circumferential surface 23 is uneven. A protrusion 25 which protrudes from the recessed portion 23a is formed on a side of the through-hole 22 closer to the tip 26 of the inner hub 9.

Note that FIG. 18 shows a portion of the outer circumferential surface 23 of the inner hub 9. An uneven portion similar to that of FIG. 18 is formed on a side (the back side of the drawing sheet) on which the other opening of the through-hole 22 is provided.

As described above, the recessed portion 23a is formed by recessing the outer circumferential surface 23 inward. Therefore, as shown in FIG. 16, a space 30 is formed between the recessed portion 23a and the inner circumferential surface of the outer hub 5. The space 30 of FIG. 16 corresponds to a portion between the protrusion 25 and the tip 26 of the inner hub 9, of the recessed portion 23a of the inner hub 9 of FIG. 18.

The protrusion 25 protruding from the recessed portion 23a in FIG. 18 is also shown in the cross-sectional view of FIG. 16. In FIG. 16, a top surface of the protrusion 25 is close to the inner circumferential surface of the outer hub 5, but is not in complete contact therewith. Therefore, a gap 31b is formed between the top surface of the protrusion 25 and the inner circumferential surface of the outer hub 5.

This holds true between a portion in which the recessed portion 23a is not formed, of the outer circumferential surface 23 of the inner hub 9, and the inner circumferential surface of the outer hub 5. The portion in which the recessed portion 23a is not formed, of the outer circumferential surface 23 of the inner hub 9, is also shown in the cross-sectional view of FIG. 17. In FIG. 17, the outer circumferential surface 23 of the inner hub 9 is close to the inner circumferential surface of the outer hub 5, but is not in complete contact therewith. Therefore, a gap 32 is formed between the outer circumferential surface 23 of the inner hub 9 and the inner circumferential surface of the outer hub 5.

With the above configuration, a liquid flowing out of the through-hole 22 flows through the gap 31b (FIG. 16), the space 30 (FIG. 16), and the gap 32 (FIG. 17) toward the tip 26 of the inner hub 9.

The flow of a liquid flowing out of the through-hole 22 will be described specifically hereinafter. Arrows "s," "t," and "g" of FIG. 18 indicate directions of the flow of the liquid flowing out of the through-hole 22. In FIG. 18, when the protrusion 25 is viewed from above, a wall surface 25a of the protrusion 25 faces the opening of the through-hole 22. In other words, the wall surface 25a forms a portion of the inner circumferential surface of the through-hole 22. Therefore, when the liquid flows out of the through-hole 22 toward the tip 26 of the inner hub 9, the liquid flow is limited by the wall surface 25a of the protrusion 25, so that the liquid is divided into streams (the arrows "s" and "t") moving on both sides of the protrusion 25. The stream in the direction indicated by the arrow "s" mostly moves in the space 30 (FIG. 16) toward the tip 26 of the inner hub 9, while the stream indicated by the arrow "t" moves around to the portion of the outer circumferential surface 23 in which the recessed portion 23a is not formed, and then flows into the gap 32 (FIG. 17).

As described above, the gap 31b is formed between the top surface of the protrusion 25 and the inner circumferential surface of the outer hub 5. Therefore, a flow (an arrow "g") occurs which enters the gap 31b and moves over the protrusion 25.

In other words, the liquid flowing out of the through-hole 22 generally moves toward the tip 26 of the inner hub 9 in the axial direction of the inner hub 9. However, the protrusion 25 limits the flow of the liquid, and therefore, the flow of the liquid moving along the circumferential direction of the inner hub 9 also is promoted.

In FIG. 14, the liquid that has reached the tip 26 of the inner hub 9 further moves toward the inside of the outer needle 7. The vicinity of the tip 26 of the inner hub 9 is not in complete contact with the inner circumferential surface of the outer hub 5, and therefore, a gap 33 is formed therebetween. A gap 34 is also formed between the hole of the outer hub 5 and the inner needle 8. A gap 35 is also formed between the inner circumferential surface of the outer needle 7 and the outer circumferential surface of the inner needle 8.

Therefore, the liquid flowing toward the tip 26 of the inner hub 9 passes through the gap 33, the gap 34, and the gap 35 and then flows out from the tip of the outer needle 7 (an arrow "h"). On the other hand, the liquid moving in the direction indicated by the arrow "d" of FIG. 16 passes through the hollow portion of the inner needle 8 and then flows out from the tip of the inner needle 8 as indicated by an arrow "i" of FIG. 14.

Therefore, by performing the above priming operation on the indwelling needle device 1B, the space and the gaps located between the through-hole 22 and the tips of the inner needle 8 and the outer needle 7 are filled with the liquid, i.e., air is removed from the space and the gaps.

Figure 19:
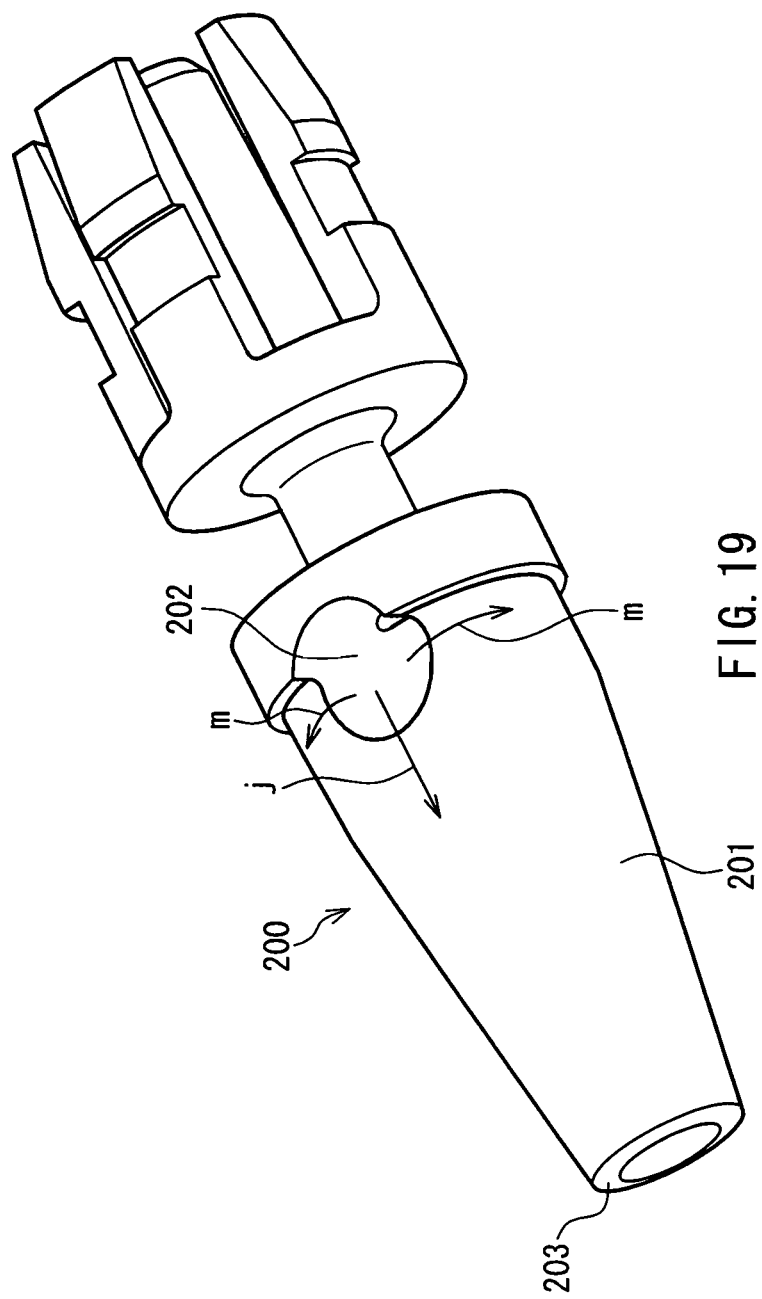
FIG. 19 is an enlarged perspective view of an inner hub 200 according to a comparative example.

Next, the inner hub 9 of the second embodiment will be described by comparing it with a comparative example. FIG. 19 is a perspective view of an inner hub 200 according to a comparative example. A through-hole 202 is formed in an even outer circumferential surface 201 of the inner hub 200, penetrating in a radial direction therethrough. Unlike the inner hub 9 of FIG. 18, neither the recessed portion 23a nor the protrusion 25 is formed in the outer circumferential surface 201 of the inner hub 200.

In the inner hub 200 of FIG. 19, a liquid from the through-hole 202 flows toward a tip 203 of the inner hub 200. Therefore, the liquid moving along a line connecting the through-hole 202 and the tip 203 forms a strong flow (an arrow "j"), and air is discharged easily along with this flow. In contrast to this, a flow (an arrow "m") in a circumferential direction of the inner hub 200 is weak. Therefore, it gradually becomes more difficult for the liquid to reach a portion which is located farther away from the opening of the through-hole 202 in the circumferential direction of the inner hub 200. Therefore, air bubbles are more likely to remain at a portion farther away from the opening of the through-hole 202 in the circumferential direction of the inner hub 200.

In the second embodiment, as described above, as shown in FIG. 18, the formation of the protrusion 25 allows the liquid flowing out from the opening of the through-hole 22 to divide into streams moving on both sides in the circumferential direction of the protrusion 25, whereby the flow moving in the circumferential direction of the inner hub 9 can be promoted. Therefore, the removal of air bubbles is promoted even in a portion distant from the opening of the through-hole 22 in the circumferential direction of the inner hub 9.

Also, as shown in FIG. 18, the opening of the through-hole 22 is interposed between the recessed portions 23a in the circumferential direction of the inner hub 9. With this configuration, the recessed portion 23a plays the role of a groove that guides the flow of the liquid in the circumferential direction of the inner hub 9, whereby the flow of the liquid moving in the circumferential direction of the inner hub 9 is promoted.

Therefore, according to the second embodiment, air reliably can be replaced with the liquid by loading the liquid using the priming operation, whereby air bubbles can be prevented from remaining on the outer circumferential surface of the inner hub 9.

Note that the shape of the protrusion 25 is not limited to that shown in FIG. 18. The protrusion 25 may have any shape as long as the liquid flowing out from the opening of the through-hole 22 and then moving toward the tip 26 of the inner hub 9 can be guided in the circumferential direction of the inner hub 9. In the second embodiment, when the protrusion 25 is viewed from above, side surfaces on both sides in the circumferential direction of the protrusion 25 are arranged to form a substantially V-shape, and therefore, the width in the circumferential direction of the protrusion 25 becomes gradually wider toward the through-hole 22. With this configuration, as described above, the wall surface 25a of the protrusion 25 can guide the liquid in the circumferential direction of the inner hub 9 immediately after the liquid flows out from the opening of the through-hole 22. In addition, the protrusion 25 has a sharp tapered tip portion (a portion C) closer to the tip 26, whereby air bubbles can be prevented from remaining at the tip portion C of the protrusion 25.

Figure 20:
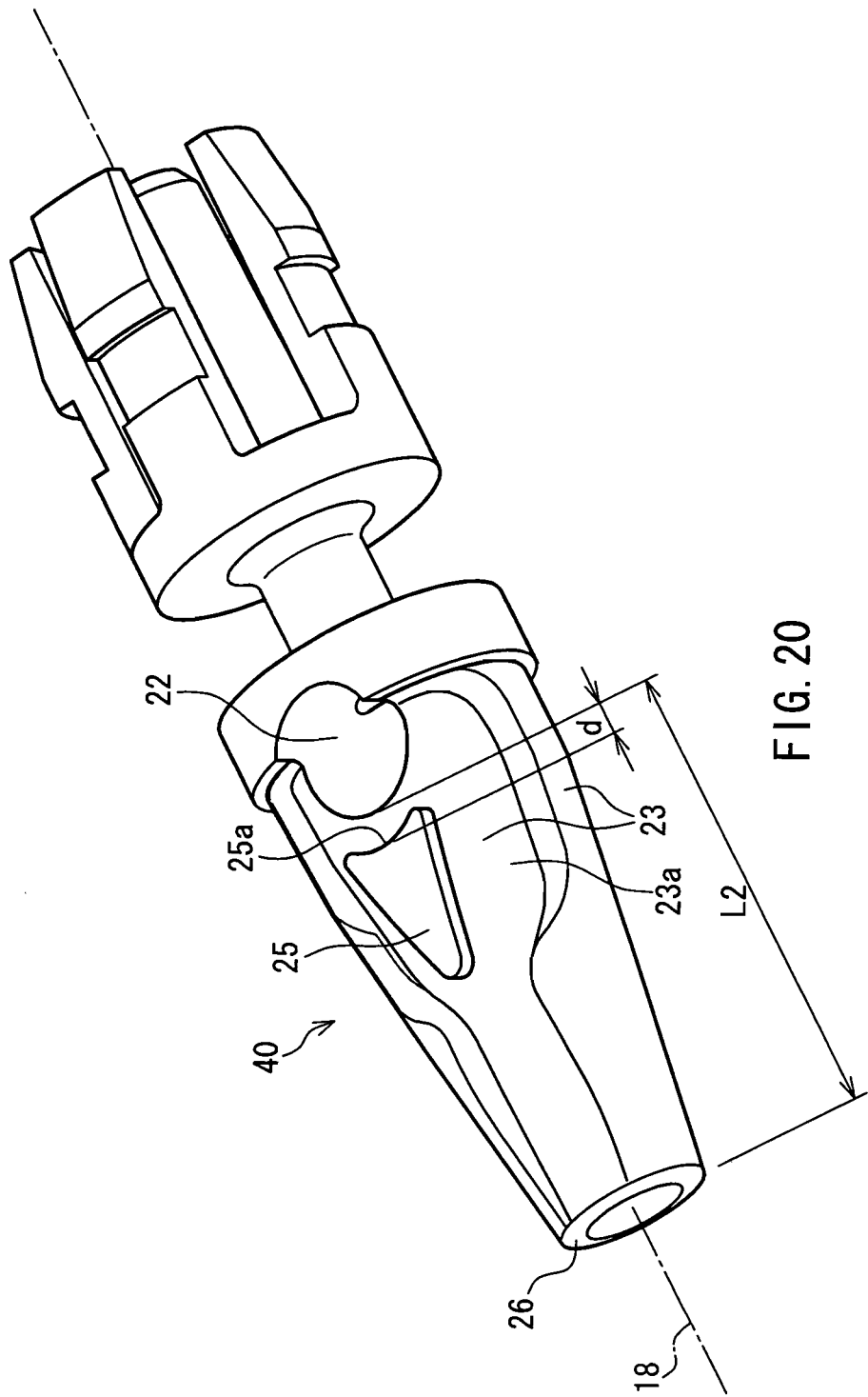
FIG. 20 is an enlarged perspective view of an inner hub 40 according to a second example of the second embodiment of the present invention.

FIG. 20 is a perspective view of an inner hub 40 according to a second example of the second embodiment. The inner hub 40 of FIG. 20 is different from the inner hub 9 of FIG. 18 in the position of the protrusion 25. In the inner hub 9 of FIG. 18, a gap is not formed between the protrusion 25 and the opening of the through-hole 22. In contrast to this, in the inner hub 40 of FIG. 19, a gap having a dimension d is formed between the protrusion 25 and the opening of the through-hole 22. The dimension d is a dimension of a gap between the protrusion 25 and the opening of the through-hole 22 on a center axis 18 of the inner hub 9 when the inner hub 9 is viewed from above.

With this configuration as well, the liquid flowing out from the opening of the through-hole 22 is limited by the wall surface 25a of the protrusion 25 closer to the through-hole 22 to divide into streams moving on both sides in the circumferential direction of the through-hole 22, whereby the flow moving in the circumferential direction of the inner hub 40 is promoted. Note that it gradually becomes more difficult for the liquid to reach and spread from the through-hole 22 in the circumferential direction as the protrusion 25 is located farther away from the opening of the through-hole 22. Therefore, the dimension d is preferably smaller than or equal to one half of a shortest distance L2 between the opening of the through-hole 22 and the tip 26 of the inner hub 9.

The embodiments described above are intended to clarify technical content of the present invention and are not intended to limit the invention to those specific examples. The present invention should be construed broadly as including all such modifications and alternatives insofar as they come within the spirit of the invention and the scope of the appended claims.

INDUSTRIAL APPLICABILITY

As described above, the needle device according to the present invention can prevent air bubbles from remaining on the outer circumferential surface of the inner hub, and therefore, is useful as, for example, a medical needle device used for infusion and blood transfusion.

DESCRIPTION OF REFERENCE CHARACTERS 1A, 1B INDWELLING NEEDLE DEVICE
2 CYLINDRICAL BODY
3 NEEDLE PORTION
4 SHIELD CYLINDER
5 OUTER HUB
7 OUTER NEEDLE
8 INNER NEEDLE
9, 40, 50, 60 INNER HUB
18 CENTER AXIS OF INNER HUB
22 THROUGH-HOLE
23, 51, 61 OUTER CIRCUMFERENTIAL SURFACE OF INNER HUB
23a, 51a, 61a RECESSED PORTION
23b SEPARATOR SURFACE
25 PROTRUSION
25a WALL SURFACE OF PROTRUSION
26, 53, 63 TIP OF INNER HUB

The invention claimed is:

1. A needle device comprising:
an inner hub with a needle attached to a tip thereof, the inner hub having a through-hole penetrating the inner hub in a radial direction, the through-hole having a first end opening and a second end opening;
a cylindrical body housing the inner hub;
first and second recessed portions formed on an outer surface of the hub, the first and second recessed portions being connected by the first end opening of the through-hole; and
third and fourth recessed portions formed on the outer surface of the hub, the third and fourth recessed portions being connected by the second end opening of the through-hole,
wherein the first and fourth recessed portions are separated by at least a first separator surface, and the second and third recessed portions are separated by at least a second separator surface, and
wherein the first recessed portion includes a portion whose depth becomes gradually shallower in a direction from the first end opening of the through-hole to the first separator surface, the second recessed portion includes a portion whose depth becomes gradually shallower in a direction from the first end opening of the through-hole to the second separator surface, the third recessed portion includes a portion whose depth becomes gradually shallower in a direction from the second end opening of the through-hole to the second separator surface, and the fourth recessed portion includes a portion whose depth becomes gradually shallower in a direction from the second end opening of the through-hole to the first separator surface.

2. The needle device according to claim 1, wherein the recessed portion is arranged to guide a liquid flowing out from the opening of the through-hole in the circumferential direction of the inner hub.

3. The needle device according to claim 1, wherein each of the first and second end openings of the through-hole interposes between the adjacent respective recessed portions in the circumferential direction of the inner hub.

4. The needle device according to claim 1, wherein the recessed portion includes a portion extending in an axial direction of the inner hub.

5. The needle device according to claim 1 wherein the width of the recessed portion is smaller than or equal to one half of the length of the opening of the through-hole in an axial direction of the inner hub.

6. The needle device according to claim 1, wherein each of the first and second separator surfaces has a greater diameter than a diameter of the respective adjacent recessed portions.

7. A needle device comprising:
an inner hub with a needle attached to a tip thereof, the inner hub including a through-hole penetrating the inner hub in a radial direction of the inner hub; and
a cylindrical body housing the inner hub; and
a protrusion formed between an opening of the through-hole and the tip of the inner hub and protruding from an outer circumferential surface of the inner hub, the protrusion having a wall surface extending in a circumferential direction and facing an opening of the through-hole,
wherein the wall surface of the protrusion is configured to change a flow direction of a liquid flowing out of the opening from an axial direction toward the tip of the inner hub to a generally circumferential direction, and
wherein when the inner hub is viewed from above, on a center axis of the inner hub, a dimension of a gap between the protrusion and the opening of the through-hole is smaller than or equal to one half of the shortest distance between the opening of the through-hole and the tip of the inner hub.

8. The needle device according to claim 7, wherein the inner hub includes a recessed portion at which the outer circumferential surface of the inner hub is recessed inward, and the protrusion protrudes from the recessed portion.

9. The needle device according to claim 8, wherein the opening of the through-hole is interposed between the recessed portions in a circumferential direction of the inner hub.

10. The needle device according to claim 7, wherein when the inner hub is viewed from above, side surfaces on both sides of the protrusion are arranged to form a substantially V-shape, and the width of the protrusion becomes gradually wider toward the through-hole.

* * * * *